| United States Patent [19] | [11] Patent Number: 4,497,650 |
| Ward et al. | [45] Date of Patent: Feb. 5, 1985 |

[54] TETRAHYDROTRIAZINES

[75] Inventors: Carl E. Ward, Mountain View, Calif.; Robert V. Berthold, South Charleston, W. Va.

[73] Assignee: Union Carbide Corporation, Danbury, Conn.

[21] Appl. No.: 108,284

[22] Filed: Dec. 28, 1979

[51] Int. Cl.³ .................. A01N 43/64; C07D 403/04
[52] U.S. Cl. ........................................ 71/93; 544/212
[58] Field of Search ............................ 71/93; 544/212

[56] References Cited

PUBLICATIONS

Martin et al., J. Prakt. Chem., vol. 321(2), 4-25-79, 315-319.

*Primary Examiner*—Catherine L. Mills
*Attorney, Agent, or Firm*—Clement J. Vicari

[57] ABSTRACT

Novel tetrahydrotriazine compounds which exhibit utility as terrestrial herbicides. Also included are herbicidal compositions containing these compounds and a method of controlling terrestrial weeds with the herbicidal compositions.

51 Claims, No Drawings

TETRAHYDROTRIAZINES

This invention relates to novel compounds and more particularly to novel tetrahydrotriazines which exhibit activity as herbicides. In another aspect the present invention relates to novel terrestrial herbicidal compositions which contain these compounds and to a method of controlling terrestrial weeds with these herbicidal compositions.

The novel compounds of the present invention are selected from the group consisting of compounds having the general formula

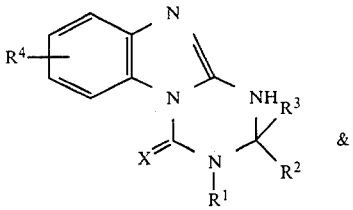

&

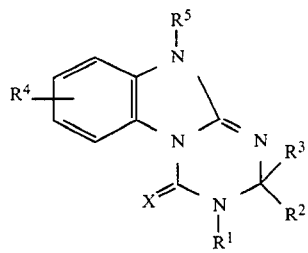

wherein $R^1$ is hydrogen, lower alkyl ($C_1$–$C_6$), cycloalkyl ($C_3$–$C_7$), lower alkenyl ($C_2$–$C_6$), loweralkynyl ($C_3$–$C_6$), haloalkyl ($C_1$–$C_6$) and alkoxyalkyl ($C_2$–$C_6$);

$R^2$ and $R^3$ individually are hydrogen, ketoalkyl ($C_3$–$C_5$), lower alkyl ($C_1$–$C_6$), cycloalkyl ($C_3$–$C_6$), alkoxyalkyl ($C_2$–$C_4$), alkenyl ($C_2$–$C_6$), haloalkyl ($C_1$–$C_6$), and acyl ($C_2$–$C_4$); $R^2$ and $R^3$ taken together can also form a spirocyclic ring of $C_3$–$C_5$ carbon atoms;

$R^4$ individually can be hydrogen, alkyl ($C_1$–$C_6$), a maximum of two halogens selected from the group consisting of Cl, F, and Br, alkoxyl ($C_1$–$C_4$), nitro, alkylthio ($C_1$–$C_4$) and alkylsulfonyl ($C_1$–$C_4$);

$R^5$ may be hydrogen, carbamoyl, N-alkylcarbamoyl ($C_2$–$C_{14}$), N-arylcarbamoyl, N-(substituted aryl)carbamoyl ($C_2$–$C_{12}$), N-carboalkoxyalkylcarbamoyl, N-haloalkylcarbamoyl ($C_2$–$C_{12}$), N-carboxyalkylcarbamoyl ($C_3$–$C_{14}$), N-alkoxyalkylcarbamoyl ($C_3$–$C_{14}$), N-arylsulfonylcarbamoyl, acyl($C_1$–$C_{14}$), aroyl, substituted aroyl, alkoxycarbonyl ($C_2$–$C_{14}$), aryloxycarbonyl, hydroxyacyl ($C_2$–$C_8$), alkoxyacyl ($C_3$–$C_9$), alkylthioacyl ($C_3$–$C_9$), alkylsulfonylacyl ($C_3$–$C_7$), N,N-dialkylaminoacyl ($C_4$–$C_{10}$), alkylsulfonyl ($C_1$–$C_{14}$), haloalkylsulfonyl ($C_1$–$C_{14}$), arylsulfonyl, substituted arylsulfonyl, alkyl ($C_1$–$C_{14}$), hydroxyalkyl ($C_1$–$C_8$), alkoxyalkyl ($C_2$–$C_9$), haloalkyl ($C_1$–$C_8$), cycloalkyl ($C_3$–$C_7$), alkenyl ($C_2$–$C_{14}$), cycloalkenyl ($C_5$–$C_7$), alkynyl ($C_2$–$C_{14}$), aryl and substituted aryl.

X is oxygen or sulfur.

Compositions falling within the above generic formula exhibit biological activity as terrestrial herbicides to a greater or lesser extent. Some exhibit very powerful herbicidal activity against terrestrial plants in extremely small dosages while others require larger dosages to be effective.

In general, the compounds which are preferred for terrestrial herbicidal activity are those of the above structural formula wherein $R^1$ is alkyl ($C_1$–$C_4$);

$R^2$ and $R^3$ individually are alkyl ($C_1$–$C_3$) and cycloalkyl ($C_3$–$C_5$);

$R^4$ is hydrogen and alkyl ($C_1$–$C_4$);

$R^5$ is hydrogen, N-alkylcarbamoyl ($C_2$–$C_{14}$), N-arylcarbamoyl, N-(substituted aryl)carbamoyl, acyl ($C_1$–$C_{14}$), alkoxycarbonyl ($C_2$–$C_{14}$), alkylsulfonyl ($C_1$–$C_{14}$), arylsulfonyl and substituted arylsulfonyl, X is 0.

Compounds which are most preferred are represented by structure and nomenclature as indicated below:

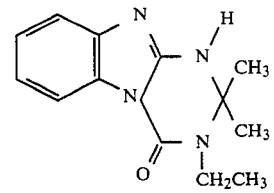

1,2-Dihydro-2,2,3-trimethyl-1,3,5-triazino[1,2-a]-benzimidazol-4(3H)-one (Compound 1)

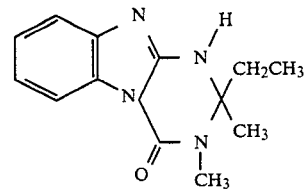

1,2-Dihydro-2,2-dimethyl-3-ethyl-1,3,5-triazino[1,2-a]-benzimidazol-4(3H)-one (Compound 2)

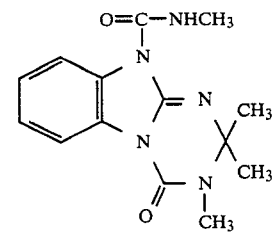

1,2-Dihydro-2,3-dimethyl-2-ethyl-1,3,5-triazino[1,2-a]-benzimidazol-4(3H)-one (Compound 3)

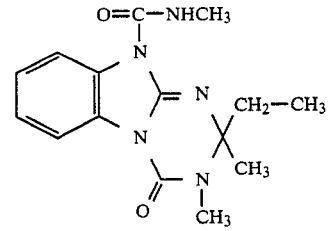

4-Oxo-2,3,4,10-tetrahydro-N,2,2,3-tetramethyl-1,3,5-triazino[1,2-a]benzimidazole-10-carboxamide (Compound 4)

2-Ethyl-4-oxo-2,3,4,10-tetrahydro-N,2,3-trimethyl-1,3,5-triazino[1,2-a]benzimidazole-10-carboxamide (Compound 5)

-continued

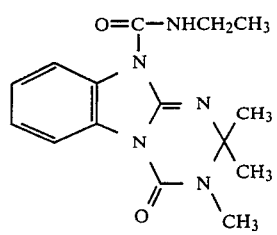

N—Ethyl-4-oxo-2,3,4,10-tetrahydro-2,2,3-trimethyl-1,3,5-triazino[1,2-a]benzimidazole-10-carboxamide (Compound 6)

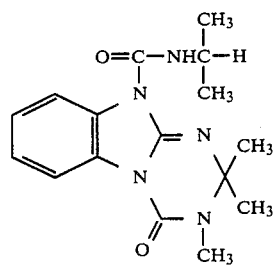

N—Isopropyl-4-oxo-2,3,4,10-tetrahydro-2,2,3-trimethyl-1,3,5-triazino[1,2-a]benzimidazole-10-carboxamide (Compound 7)

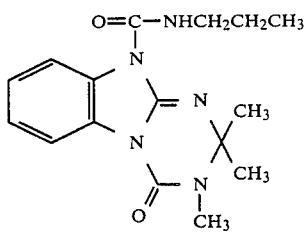

N—Propyl-4-oxo-2,3,4,10-tetrahydro-2,2,3-trimethyl-1,3,5-triazino[1,2-a]benzimidazole-10-carboxamide (Compound 8)

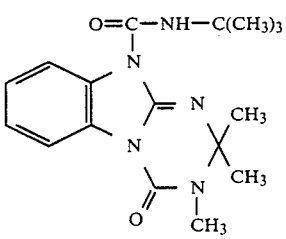

N—tert-Butyl-4-oxo-2,3,4,10-tetrahydro-2,2,3-trimethyl-1,3,5-triazino[1,2-a]benzimidazole-10-carboxamide (Compound 9)

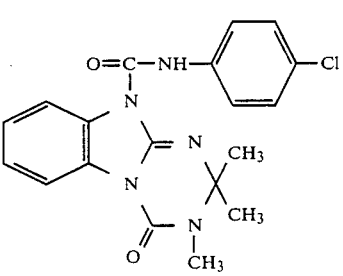

N—(4-Chlorophenyl)-4-oxo-2,3,4,10-tetrahydro-2,2,3-trimethyl-1,3,5-triazino[1,2-a]benzimidazole-10-carboxamide (Compound 10)

-continued

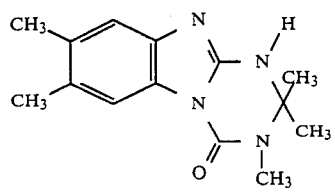

1,2-Dihydro-2,2,3,7,8-pentamethyl-1,3,5-triazino-[1,2-a]benzimidazol-4(3H)-one (Compound 11)

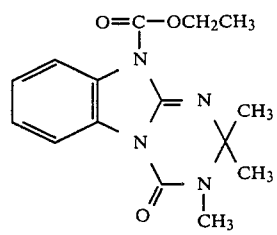

2,10-Dihydro-10-(ethoxycarbonyl)-2,2,3-trimethyl-1,3,5-triazino[1,2-a]benzimidazol-4(3H)-one (Compound 12)

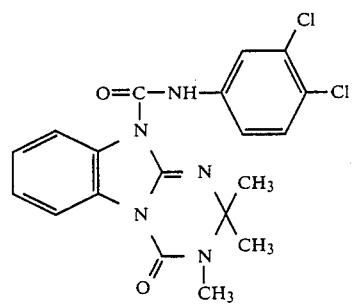

N—(3,4-Dichlorophenyl)-4-oxo-2,3,4,10-tetrahydro-2,2,3-trimethyl-1,3,5-triazino[1,2-a]benzimidazole-10-carboxamide (Compound 13)

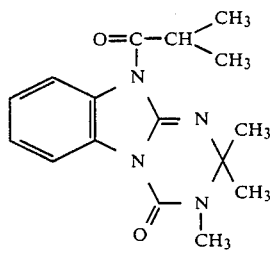

2,10-Dihydro-10-[(2-methyl)propanoyl]-2,2,3-trimethyl-1,3,5-triazino[1,2-a]benzimidazol-4(3H)-one (Compound 14)

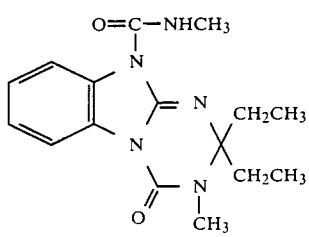

2,2-Diethyl-N,3-dimethyl-4-oxo-2,3,4,10-tetrahydro-1,3,5-triazino[1,2-a]benzimidazole-10-carboxamide (Compound 15)

-continued

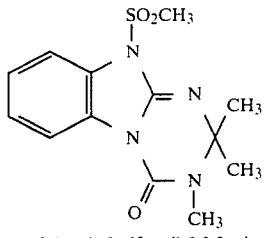

2,10-Dihydro-10-(methylsulfonyl)-2,2,3-trimethyl-1,3,5-triazino[1,2-a]benzimidazol-4(3H)-one (Compound 16)

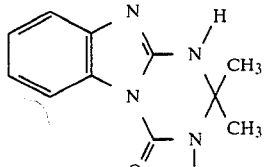

1,2-Dihydro-2,2-dimethyl-1,3,5-triazino[1,2-a]-benzimidazol-4(3H)-one (Compound 17)

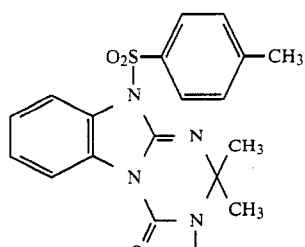

2,10-Dihydro-10-[(4-tolyl)sulfonyl]-2,2,3-trimethyl-1,3,5-triazino[1,2-a]benzimidazol-4(3H)-one (Compound 18)

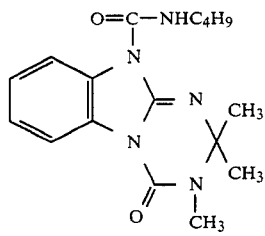

N—Butyl-4-oxo-2,3,4,10-tetrahydro-2,2,3-trimethyl-1,3,5-triazino[1,2-a]benzimidazole-10-carboxamide (Compound 19)

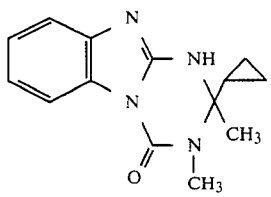

2-Cyclopropyl-1,2-dihydro-2,3-dimethyl-1,3,5-triazino[1,2-a]benzimidazol-4(3H)-one (Compound 20)

For convenience the $R^1$–$R^5$ substituents of the preferred compounds within the generic formula are as indicated in the following Table I.

TABLE I

| Compound | $R^1$ | $R^2$ | $R^3$ | $R^4$ | $R^5$ |
|---|---|---|---|---|---|
| 1 | $CH_3$ | $CH_3$ | $CH_3$ | —* | — |
| 2 | $C_2H_5$ | $CH_3$ | $CH_3$ | — | — |
| 3 | $CH_3$ | $CH_3$ | $C_2H_5$ | — | — |
| 4 | $CH_3$ | $CH_3$ | $CH_3$ | — | $CH_3NHCO-$ |
| 5 | $CH_3$ | $CH_3$ | $C_2H_5$ | — | $CH_3NHCO-$ |
| 6 | $CH_3$ | $CH_3$ | $CH_3$ | — | $C_2H_5NHCO-$ |
| 7 | $CH_3$ | $CH_3$ | $CH_3$ | — | $(CH_3)_2CHNHCO-$ |
| 8 | $CH_3$ | $CH_3$ | $CH_3$ | — | $n\text{-}C_3H_7NHCO-$ |
| 9 | $CH_3$ | $CH_3$ | $CH_3$ | — | $(CH_3)_3CNHCO-$ |
| 10 | $CH_3$ | $CH_3$ | $CH_3$ | — | Cl—⟨⟩—NHCO— |
| 11 | $CH_3$ | $CH_3$ | $CH_3$ | 7,8-$(CH_3)_2$ | — |
| 12 | $CH_3$ | $CH_3$ | $CH_3$ | — | $C_2H_5OCO-$ |
| 13 | $CH_3$ | $CH_3$ | $CH_3$ | — | Cl,Cl—⟨⟩—NHCO— |
| 14 | $CH_3$ | $CH_3$ | $CH_3$ | — | $(CH_3)_2CHCO-$ |
| 15 | $CH_3$ | $C_2H_5$ | $C_2H_5$ | — | $CH_3NHCO-$ |
| 16 | $CH_3$ | $CH_3$ | $CH_3$ | — | $CH_3SO_2-$ |
| 17 | H | $CH_3$ | $CH_3$ | — | — |
| 18 | $CH_3$ | $CH_3$ | $CH_3$ | — | $CH_3-$⟨⟩$-SO_2-$ |
| 19 | $CH_3$ | $CH_3$ | $CH_3$ | — | $n\text{-}C_4H_9NHCO-$ |
| 20 | $CH_3$ | ▷ | $CH_3$ | — | — |

*— designates hydrogen

In general, the novel tetrahydrotriazines of this invention can be prepared according to several methods illustrated by the following reaction schemes:

Method I

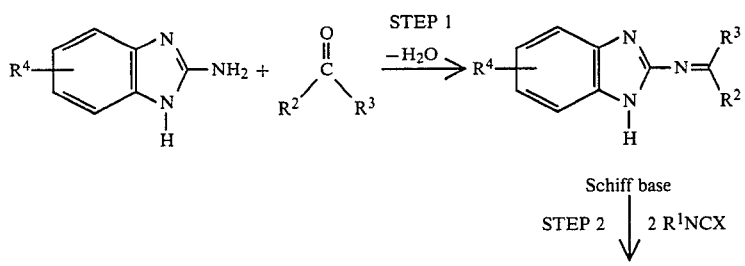

Method I

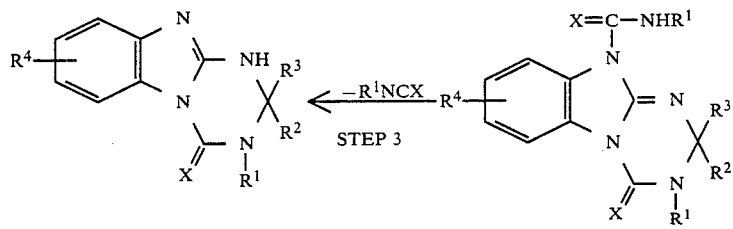

where X, and $R^1$–$R^4$ are as described previously.

A special case of Method I is that in which $R^1$=hydrogen and X=oxygen. In this case the isocyanic acid (HNCO) required for the second step is generated in situ by addition to the reaction mixture of N-chloroformamide as shown below:

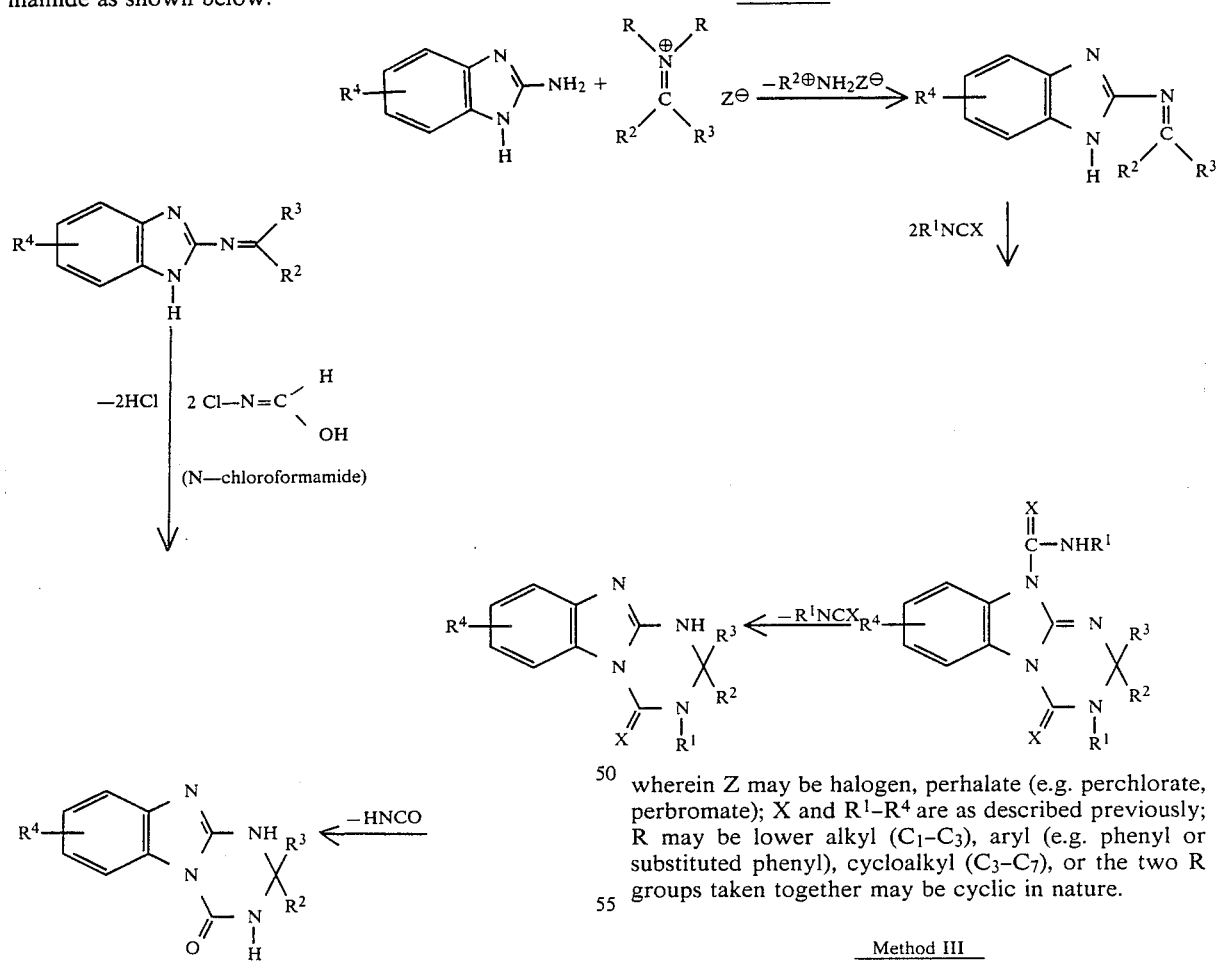

wherein Z may be halogen, perhalate (e.g. perchlorate, perbromate); X and $R^1$–$R^4$ are as described previously; R may be lower alkyl ($C_1$–$C_3$), aryl (e.g. phenyl or substituted phenyl), cycloalkyl ($C_3$–$C_7$), or the two R groups taken together may be cyclic in nature.

Method III

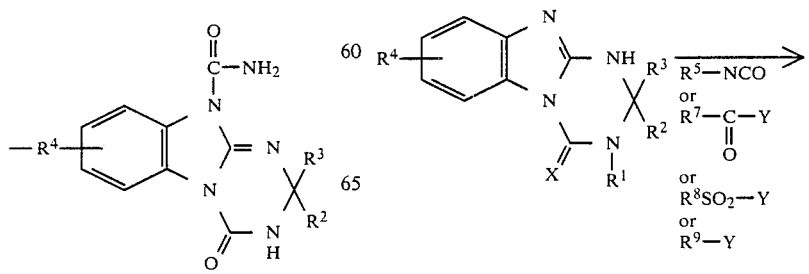

-continued
Method III

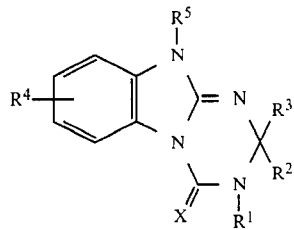

wherein X and $R^1$–$R^5$ are as defined previously; $R^6$ may be alkyl ($C_1$–$C_{14}$), aryl, substituted aryl, carboalkoxyalkyl, alkoxyalkyl, or hydrogen; $R^7$ may be alkyl ($C_1$–$C_{14}$), alkoxyalkyl, alkylthioalkyl, alkylsulfonylalkyl, dialkylaminoalkyl, aryl, cycloalkyl, substituted aryl, alkoxy ($C_1$–$C_{14}$), aryloxy, substituted aryloxy; $R^8$ may be alkyl ($C_1$–$C_{14}$), aryl, substituted aryl; $R^9$ may be alkyl ($C_1$–$C_{14}$), alkoxyalkyl, alkylthioalkyl, alkylsulfonylalkyl, dialkylaminoalkyl, aryl, cycloalkyl ($C_3$–$C_7$), alkenyl ($C_2$–$C_{14}$), cycloalkenyl ($C_5$–$C_7$), alkynyl ($C_2$–$C_{14}$); Y may be halogen (e.g. chlorine, bromine, iodine), arylsulfonate, alkylsulfonate.

In general, Method I involves three steps in the procedure for obtaining the final product, i.e. step 1, which is a Schiff base-forming reaction; step 2 which is a ring forming reaction involving the Schiff base formed in step 1; and step 3 which is a thermal or hydrolytic cleavage step to form the tetrahydrotriazine.

The step 1 Schiff base-forming reaction illustrated in Method I utilizes an appropriate substituted amine which is admixed with an appropriate ketone as indicated. The reaction is conducted in the presence of a solvent which advantageously can be the ketone reactant itself or alternatively the ketone can be employed with a cosolvent. Illustrative of solvents that can be utilized in the conduct of the Schiff base-forming reaction are tetrahydrofuran, dioxane and dimethoxyethane. The Schiff base-forming reaction step of Method I can be conducted in the temperature range of about 20°–200° C., preferably about 35° C. to 120° C. and in the pressure range of one atmosphere up to that required to contain the reaction at about 200° C. The concentration of the amine starting material in the mixture before reaction begins can be from 0.01 to 1.0 molar, preferably about 0.1 to 0.7 molar. In addition, the Schiff base-forming reaction step can, if desired, be conducted in the presence of an acid catalyst. Suitable acid catalysts include p-toluenesulfonic acid, trifluoroacetic acid, or zinc chloride.

As will be observed from the reaction scheme illustrated in Method I, it is necessary to remove the water formed as a by-product in the reaction. Water can be removed from the reaction by adding a drying agent or water scavenger to the reaction mixture. Illustrative of drying agents which can be used include molecular sieves (3A, 4A and 5A), calcium sulfate, calcium chloride and magnesium sulfate. Water may also be removed from the reaction by azeotropic distillation using a suitable cosolvent, examples of which include benzene, toluene and xylene. The Schiff base formed in Method I can be isolated or alternatively it can be subjected to the ring-forming reaction (step 2) in situ. If the Schiff base is isolated, it is thereafter subsequently dissolved in a suitable solvent and is then subjected to the illustrated ring-forming reaction. Examples of suitable solvents for this purpose include tetrahydrofuran, acetone, dioxane, dimethoxyethane, chloroform and methylene chloride. The ring-forming step of Method I can be conducted using from two to ten molar equivalents of a suitable isocyanate or isothiocyanate based on the number of moles of starting amine employed. In general, the ring-forming reaction step is conducted at a temperature range of about 0°–200° C., preferably about 25° to 80° C., and in a pressure range of about one atmosphere up to that required to contain the reaction at 200° C. The cleavage step 3 illustrated in Method I can be accomplished either hydrolytically or thermolytically. When the thermolytic method is used, the cyclized material from step 2 is placed in a suitable solvent; the resulting mixture is thereafter heated and the cleaved isocyanate is distilled from the mixture. Illustrative of the solvents utilized for the thermal cleavage step include petroleum hydrocarbons, xylene, diglyme and dimethylsulfoxide. The thermolytic cleavage of $R^1NCX$ may also occur during recovery of product from the ring-forming reaction (step 2) when, as may be practiced, the crude product is continually extracted with a hot inert solvent (such as hexane) as in a Soxhlet extraction system. Such a spontaneous thermolytic cleavage of $R^1NCX$ during workup frequently results in isolation of the final cleavage product alone, or of mixtures of the final product with the 10-N-carbamoylated precursor. The thermolytic reaction step 3 can be conducted at a temperature range of about 80°–250° C., preferably about 100° to 180° C., and in a pressure range of about 0.2–2.0, preferably 0.5 to 1.0 atmosphere. When the hydrolytic method is utilized, the cyclized material from step 2 is dissolved in a suitable solvent and the resulting solution is treated with water and an acid or base catalyst. Suitable solvents for the hydrolytic method include tetrahydrofuran, dioxane, acetone, dimethoxyethane and ethanol. Suitable acid catalysts include hydrochloric acid, sulfuric acid, trifluoroacetic acid and p-toluenesulfonic acid. Suitable base catalysts include sodium hydroxide, sodium carbonate, potassium hydroxide, potassium carbonate or triethylamine. The hydrolytic method can be conducted in a temperature range of about 0°–100° C., preferably about 25° to 60° C., and in the pressure range of one atmosphere up to that required to contain the reaction at 100° C.

The Schiff base-forming reaction illustrated in Method II can be conducted using a stoichiometric amount (i.e. one equivalent) of the iminium salt in a suitable solvent. Suitable solvents include tetrahydrofuran, dioxane, and dimethoxyethane. Alternatively, the Schiff base-forming reaction of Method II can be conducted using a catalytic amount of the iminium salt in an appropriate solvent. The appropriate solvent is the ketone $R^2COR^3$ or a mixture of this ketone and a suitable cosolvent. Suitable cosolvents include tetrahydrofuran, dioxane or dimethoxyethane. The Schiff base-forming reaction of Method II can be conducted in a temperature range of about 20°–200° C., preferably 35°–100° C., and in a pressure range of about 0.2 atmosphere up to that required to contain the reaction at about 200° C. The concentration of the starting material (amine) in the mixture before reaction begins may be from 0.01 to 1.0, preferably 0.1 to 0.7 molar. The Schiff base formed in Method II can be isolated or alternatively subjected to the ring-forming step in situ. Conditions for reaction in the ring-forming step and the subsequent cleavage step are as discussed for Method I.

The reaction illustrated by Method III represents the introduction of the substituent $R^5$ (when $R^5$ is other than hydrogen). This step can be conducted by combining the appropriate tricyclic material, obtained by Methods I and II, with the appropriate organic isocyanate, acyl halide, aroyl halide, sulfonyl halide or halide as defined previously in a suitable organic solvent in the presence of a suitable base catalyst or acid acceptor. Suitable organic solvents include acetone, tetrahydrofuran, dioxane, dimethoxyethane, methylene chloride and chloroform. Suitable catalysts or acid acceptors include triethylamine, pyridine, sodium carbonate, and potassium carbonate. The reaction may be conducted in the temperature range of 0°–100° C., preferably 25° to 50° C., and in the pressure range of 0.5–10.0, preferably 1 to 2 atmospheres. The concentration of the tricyclic material before reaction may be from 0.01–1.0, preferably 0.05 to 0.5 molar.

In general (for Methods I and II) the starting amines and their coreactants are known compounds or may be prepared through well-established chemical transformations. For example the 2-aminobenzimidazole reactant can be prepared by reaction of ortho-phenylenediamines with cyanamide according to the procedure of S. Weiss et al, ANGEWANDTE CHEMIE INTERNATIONAL EDITION, Volume 12, page 841 (1973).

The ketones can be prepared by oxidation of the corresponding secondary alcohols as described by Arnold P. Lurie in KIRK-OTHMER ENCYCLOPEDIA OF CHEMICAL TECHNOLOGY, Second Edition, Volume 12, page 125, John Wiley and Sons, New York.

The following terrestrial herbicidally active compounds are further illustrative of compounds within the purview of the above generic formula and which can be conveniently prepared by the methods of the invention simply by selecting appropriate reactants for use in the procedures described previously:

7,8-Dichloro-4-oxo-2,3,4,10-tetrahydro-N,2,2,3-tetramethyl-1,3,5-triazino[1,2-a]benzimidazole-10-carboxamide
1,2-Dihydro-8-nitro-2,2,3-trimethyl-1,3,5-triazino[1,2-a]benzimidazol-4(3H)-one
4-Oxo-N,2,2,3,8-pentamethyl-2,3,4,10-tetrahydro-1,3,5-triazino[1,2-a]benzimidazole-10-carboxamide
1,2-Dihydro-2,2,3,9-tetramethyl-1,3,5-triazino[1,2-a]benzimidazol-4(3H)-one
1,2-Dihydro-2,2,3,7-tetramethyl-1,3,5-triazino[1,2-a]benzimidazol-4(3H)-one
7,8-Dichloro-1,2-dihydro-1,3,5-triazino[1,2-a]benzimidazol-4(3H)-one
1,2-Dihydro-3-isopropyl-1,3,5-triazino[1,2-a]benzimidazol-4(3H)-one
2,2-Diethyl-1,2-dihydro-1,3,5-triazino[1,2-a]benzimidazol-4(3H)-one
1,2-Dihydro-2,3,7,8-tetramethyl-2-trifluoromethyl-1,3,5-triazino[1,2-a]benzimidazol-4(3H)-one
1,2-Dihydro-7-ethoxy-2,2,3-trimethyl-1,3,5-triazino-[1,2-a]benzimidazol-4(3H)-one
1,2-Dihydro-2,2,3,8-tetramethyl-1,3,5-triazino[1,2-a]benzimidazol-4(3H)-one
2,2-Bis(trifluoromethyl)-1,2-dihydro-3-methyl-1,3,5-triazino[1,2-a]benzimidazol-4(3H)-one
1,2-Dihydro-2,3-dimethyl-2-trifluoromethyl-1,3,5-triazino[1,2-a]benzimidazol-4(3H)-one
1,2-Dihydro-2,2-dimethyl-3-trifluoromethyl-1,3,5-triazino[1,2-a]benzimidazol-4(3H)-one
1,2-Dihydro-2,3-dimethyl-1,3,5-triazino[1,2-a]benzimidazol-4(3H)-one
2,10-Dihydro-10-[(trifluoromethyl)sulfonyl]-2,2,3-trimethyl-1,3,5-triazino[1,2-a]benzimidazol-4(3H)-one
1,2-Dihydro-2-ethyl-2-methyl-1,3,5-triazino[1,2-a]-benzimidazol-4(3H)-one
4-Oxo-2,3,4,10-tetrahydro-N,2,3-trimethyl-1,3,5-triazino[1,2-a]benzimidazole-10-carboxamide
1,2-Dihydro-2-propyl-1,3,5-triazino[1,2-a]benzimidazol-4(3H)-one
1,2-Dihydro-2-isopropyl-1,3,5-triazino[1,2-a]benzimidazol-4(3H)-one
1,2-Dihydro-3-propyl-1,3,5-triazino[1,2-a]benzimidazol-4(3H)-one
N,3-Dipropyl-4-oxo-2,3,4,10-tetrahydro-1,3,5-triazino[1,2-a]benzimidazole-10-carboxamide
1,2-Dihydro-2,7-dimethyl-1,3,5-triazino[1,2-a]benzimidazol-4(3H)-one
1,2-Dihydro-2,2,8-trimethyl-1,3,5-triazino[1,2-a]-benzimidazol-4(3H)-one
1,2-Dihydro-2,2,7,8-tetramethyl-1,3,5-triazino[1,2-a]-benzimidazol-4(3H)-one
1,2-Dihydro-3-ethyl-2-methyl-1,3,5-triazino[1,2-a]-benzimidazol-4(3H)-one
3-Cyclopropyl-1,2-dihydro-2-methyl-1,3,5-triazino-[1,2-a]benzimidazol-4(3H)-one
1,2-Dihydro-2-methyl-2-vinyl-1,3,5-triazino[1,2-a]-benzimidazol-4(3H)-one
1,2-Dihydro-2-(2-propenyl)-1,3,5-triazino[1,2-a]-benzimidazol-4(3H)-one
2-Acetyl-1,2-dihydro-2,3-dimethyl-1,3,5-triazino[1,2-a]benzimidazol-4(3H)-one
1,2-Dihydro-2,3-dimethyl-2-(2-oxopropyl)-1,3,5-triazino[1,2-a]benzimidazol-4(3H)-one
1,2-Dihydro-2-methoxymethyl-2-methyl-1,3,5-triazino[1,2-a]benzimidazol-4(3H)-one The following Examples will more fully ilustrate the invention. In Example 1, the procedures described are representative of those used to prepare benzimidazotetrahydro-s-triazines and their 10-N substituted derivatives. At the end of the Examples is Table II which indicates the $R^1$–$R^5$ and X values of each Example.

EXAMPLE 1

4-Oxo-2,3,4,10-tetrahydro-N,2,2,3-tetramethyl-1,3,5-triazino[1,2-a]benzimidazole-10-carboxamide (1A) and 1,2-Dihydro-2,2,3-trimethyl-1,3,5-triazino [1,2-a]benzimidazol-4(3H)-one(1B)

A 1-liter, round bottomed flask containing a magnetic stirrer bar was charged with 16 g (0.12 mole) of 2-aminobenzimidazole, 500 ml of acetone and 16 g of 3A molecular sieves. The flask was fitted with a reflux condenser bearing a $CaSO_4$-drying tube after which the reaction mixture was stirred and heated at reflux. An additional 8 g of sieves were added on the second and fifth days of heating. Aliquots of the reaction mixture were withdrawn at 24 hour intervals, filtered, concentrated in vacuo and examined by NMR spectroscopy. After seven days the reaction was 58% complete. The reaction mixture was cooled to room temperature and methyl isocyanate (13.7 g, 0.24 mole) was added rapidly via syringe. The resulting mixture was stirred overnight at room temperature after which time it was concentrated under reduced pressure to afford a brittle solid. The solid was broken up, slurried in a hexane and transferred into a Soxhlet extraction thimble. The thimble was placed in an extractor fitted to a 500-ml, round-bottomed flask containing a magnetic stirring bar and 400 ml of hexane. The material in the thimble was extracted until TLC (silica, 80:2:1, CHCl$_3$:MeOH:NH$_4$OH) showed none of the desired products remained (from 2-6 da.). The solids which had precipitated in the extraction pot were collected with suction and the resulting filtrate was concentrated to provide an additional small amount of material. The combined solids consisted of 14.9 g of a mixture of 1,2-dihydro-2,2,3-trimethyl-1,3,5-triazino[1,2-a]benzimidazol-4(3H)-one and its 10-N-methylcarbamoyl precursor 4-oxo-2,3,4,10-tetrahydro-N,2,2,3-tetramethyl-1,3,5-triazino[1,2-a]benzimidazole-10-carboxamide ($\geq 0.052$ mole of tricyclic products; $\geq 43\%$ yield).

The mixture was charged to a 500 ml, round-bottom flask containing a magnetic stirring bar. THF (300 ml) was added followed by 30 ml of 10% aqueous sodium hydroxide. The resulting heterogeneous mixture was stirred at room temperature for 6.5 hr. after which time TLC showed that only a trace of the 10-N-methylcarbamoyl material remained. The reaction mixture was transferred to a separatory funnel and washed with brine (3X). The organic phase was dried over potassium carbonate and concentrated under reduced pressure to afford 11.6 g of crude product 1B as a brown solid (42% yield based on 2-aminobenzimidazole). This material was recrystallized from acetone to yield 6.9 g of pure material (1B). An analytical sample prepared as described above sintered at 206° and had mp 209° C. (dec).

Anal. Calcd. for C$_{12}$H$_{14}$N$_4$O: C, 62.59; H, 6.13; N, 24.33. Found: C, 62,47; H, 6.16; N, 24.24.

Spectral data: nmr ($\delta$, CDCl$_3$) 1.73 (S, 6H, gem. methyls), 3.12 (S, 3H, N-CH$_3$), 6.96-7.40 (m, 3H, aromatic H), 7.83-8.16 (m, 1H, C-6 aromatic H); ir ($\nu_{max}^{CHCl_3}$) 31-3200 (broad, NH str.), 1710 (C=O str.), 1660 (C=N str.), 1620, 1600, 1500, 1460, 1420, 1380, 1310, 1290, 1230, 1170, 1140, 1100, 1050, 890 cm$^{-1}$; uv ($\lambda_{max}^{EtOH}$) 282 nm ($\epsilon$ 7600), 287 nm ($\epsilon$ 7830).

EXAMPLE 2

1,2-Dihydro-2,2-dimethyl-3-ethyl-1,3,5-triazino[1,2-a]benzimidazol-4(3H)-one

The title compound was prepared from 2-aminobenzimidazole, acetone and ethyl isocyanate by the procedure described in the first paragraph of Example 1. In this preparation, a 10-N-methylcarbamoyl derivative was not isolated and the subject compound was recovered from the Soxhlet extraction and recrystallized from acetone to give a solid, mp above 300° C. (dec). The confirmatory elemental analysis is shown in Table III.

EXAMPLE 3

2,2-Dimethyl-N,3-dipropyl-4-oxo-2,3,4,10-tetrahydro-1,3,5-triazino[1,2-a]benzimidazole-10-carboxamide The subject compound was prepared by reaction of 2-aminobenzimidazole, acetone and propyl isocyanate with workup all essentially as described in the first paragraph of Example 1. The product was purified by column chromatography on silica, eluting with chloroform, giving, on evaporation, white crystals, mp 72°-74° C. The confirmatory elemental analysis is shown in Table III.

EXAMPLE 4

1,2-Dihydro-2,2-dimethyl-3-propyl-1,3,5-triazino[1,2-a]benzimidazol-4(3H)-one

The title compound was prepared by hydrolysis of the precursor compound of Example 3 in the presence of 10% aqueous sodium hydroxide and THF employing the method of paragraph 2, Example 1. The product was crystallized from acetone to give colorless prisms, mp 170° C. (dec). The confirmatory elemental analysis is shown in Table III.

EXAMPLE 5

3-Butyl-1,2-dihydro-2,2-dimethyl-1,3,5-triazino[1,2-a]benzimidazol-4(3H)-one

The title compound was prepared from 2-aminobenzimidazole, acetone, and n-butyl isocyanate, conducting the initial condensation and subsequent base hydrolysis of the intermediate 10-N-butylcarbamoyl precursor as described in Example 1. The solid product had mp 142°-149° C. (dec.). The confirmatory elemental analysis is shown in Table III.

EXAMPLE 6

1,2-Dihydro-2,2-dimethyl-1,3,5-triazino[1,2-a]benzimidazol-4(3H)-one

A mixture of 16 g (0.12 mole) of 2-aminobenzimidazole, 100 ml of acetone and 16 g of 3A molecular sieves was stirred and heated under reflux, adding 8 g of additional sieves after 24 hours. Refluxing was continued for a total period of 3 days, after which the mixture was allowed to cool and a solution of 4.77 g (0.06 mole) of N-chloroformamide[1] in ~25 ml. of acetone added dropwise with stirring. The mixture was warmed to the reflux point several times and the rate of N-chloroformamide addition adjusted to keep the temperature just below the reflux point. An additional 50 ml of acetone were added to facilitate stirring of the thickening reaction mixture. Upon completion of the feed, the reaction flask was fitted with a drying tube and the mixture stirred for 3 days at room temperature. The reaction mixture was then evaporated under reduced pressure to give 9.3 g of a tan solid. The latter was extracted with boiling acetone to separate an insoluble fraction and the acetone solution evaporated to give the crude solid product. The latter material was chromatographed on silica, eluting with CHCl$_3$/CH$_3$OH (80:5). Fractions 3 through 8 were combined and evaporated to give 3.9 g of product, mp 178°-180° C. (dec).

[1] N-Chloroformamide was prepared by the procedure described in U.S. Pat. No. 4,022,825, May 10, 1977.

Anal. Calcd. for C$_{11}$H$_{12}$N$_4$O: C, 61.09; H, 5.60; N, 25.91. Found: C, 61.00; H, 5.49; N, 25.38.

Spectral data: nmr ($\delta$ d$_6$DMSO) 1.50 (S, 6H), 6.87-7.47 (m, 3H), 7.63-7.97 (m, 1H), 8.58 (broad, 2H); ir ($\nu_{max}^{KBr}$) 3400 (broad), 3225, 3075, 2975, 2875, 1720, 1630, 1600, 1580, 1460, 1375, 1290, 1270, 1230, 1180, 1140, 1010, 760, 740 cm$^{-1}$.

EXAMPLE 7

2,2-Dimethyl-N,3-diisopropyl-4-oxo-2,3,4,10-tetrahydro-1,3,5-triazino[1,2-a]benzimidazole-10-carboxamide The title compound was prepared from 2-aminobenzimidazole, acetone and isopropyl isocyanate employing the method of the first paragraph of Example 1. The product was purified by column chromatography on silica, eluting with chloroform to give a white solid, mp

EXAMPLE 8

2-Ethyl-4-oxo-2,3,4,10-tetrahydro-N,2,3-trimethyl-1,3,5-triazino[1,2-a]benzimidazole-10-carboxamide The title compound was prepared from 2-aminobenzimidazole, methyl ethyl ketone and methyl isocyanate employing the procedure of the first paragraph of Example 1. The product was purified by column chromatography, developing with chloroform/methanol (97%/2.4% by volume), giving a tan solid, mp 113°–119° C. (dec.). The confirmatory elemental analysis is shown in Table III.

EXAMPLE 9

1,2-Dihydro-2,3-dimethyl-2-ethyl-1,3,5-triazino[1,2-a]benzimidazol-4(3H)-one

The 10-N-methylcarbamoyl precursor prepared in Example 8 was hydrolyzed in the presence of 10% aqueous sodium hydroxide and THF according to the procedure of paragraph 2, Example 1. The product was obtained as crystals from acetone, mp 202° C. (dec). The confirmatory elemental analysis is shown in Table III.

EXAMPLE 10

3-Butyl-4-oxo-2,3,4,10-tetrahydro-N,2,2-trimethyl-1,3,5-triazino[1,2-a]benzimidazole-10-carboxamide by carbamoylation of the parent heterocycle 3-Butyl-1,2-dihydro-2,2-dimethyl-1,3,5-triazino[1,2-a]benzimidazol-4(3H)-one (2.5 g, 0.0092 mole) from Example 5 was suspended in a solution of triethylamine (0.5 ml) in 50 ml of acetone. The resulting mixture was stirred with a magnetic stirring bar, and 0.54 ml (0.0092 mole) of methyl isocyanate added, in one portion, by a syringe. The resulting mixture was stirred at room temperature, becoming a yellow solution after about 10 minutes, and stirring was continued overnight. Solvent was removed from the mixture under reduced pressure and the resulting solid chromatographed on a silica column giving 1.8 g of title compound, mp 124°–129° C.

Anal. Calcd. for $C_{17}H_{23}N_5O_2$: C, 61.99; H, 7.04; N, 21.26. Found: C, 62.11; H, 7.04; N, 21.16.

Spectral data: nmr ($\delta$, $CDCl_3$) 0.70–1.13 (m, 3H, butyl $CH_3$), 1.13–1.83 (m, 10H, $CH_3-C-CH_3$ and $C-CH_2CH_2-C$), 2.98 (d, 3H, J=4Hz, N—$CH_3$), 3.13–3.67 (m, 2H, N—$CH_2$—), 6.97–7.33 (m, 2H, aromatic H), 7.77–8.10 (m, 1H, aromatic H), 8.10–8.43 (m, 1H, aromatic), 9.03–9.55 (broad, 1H, NH); ir ($\nu_{max}^{CHCl_3}$) 3225, 2960, 2975, 1710, 1660, 1470, 1390, 1370, 1310, 1290, 1190, 1160, 1040, 1020, 970, 930 $cm^{-1}$.

EXAMPLE 11

N-Ethyl-4-oxo-2,3,4,10-tetrahydro-2,2,3-trimethyl-1,3,5-triazino[1,2-a]benzimidazole-10-carboxamide The title compound was prepared by reaction of 1,2-dihydro-2,2,3-trimethyl-1,3,5-triazino[1,2-a]benzimidazol-4(3H)-one (see Example 1 (B)) with ethyl isocyanate according to the general procedure of Example 10. The product, mp 127°–131° C., was obtained as a white solid in 96% yield. The confirmatory elemental analysis is shown in Table III.

EXAMPLE 12

N-Propyl-4-oxo-2,3,4,10-tetrahydro-2,2,3-trimethyl-1,3,5-triazino[1,2-a]benzimidazole-10-carboxamide The title compound was prepared from 1,2-dihydro-2,2,3-trimethyl-1,3,5-triazino[1,2-a]benzimidazol-4(3H)-one (Example 1 (B)) and n-propyl isocyanate according to the procedure of Example 10. The confirmatory elemental analysis for the product, mp 85°–87° C., is shown in Table III.

EXAMPLE 13

N-Isopropyl-4-oxo-2,3,4,10-tetrahydro-2,2,3-trimethyl-1,3,5-triazino[1,2-a]benzimidazole-10-carboxamide The procedure of Example 10 was used to prepare the title compound from 1,2-dihydro-2,2,3-trimethyl-1,3,5-triazino[1,2-a]benzimidazol-4(3H)-one and isopropyl isocyanate. The product crystallized as a white solid, mp 93°–96° C. The confirmatory elemental analysis is shown in Table III.

EXAMPLE 14

N-Butyl-4-oxo-2,3,4,10-tetrahydro-2,2,3-trimethyl-1,3,5-triazino[1,2-a]benzimidazole-10-carboxamide The procedure of Example 10 was used to prepare the title compound from 1,2-dihydro-2,2,3-trimethyl-1,3,5-triazino[1,2-a]benzimidazol-4(3H)-one and n-butyl isocyanate. The confirmatory elemental analysis for the product, mp 95°–97° C., is shown in Table III.

EXAMPLE 15

N-(4-Chlorophenyl)-4-oxo-2,3,4,10-tetrahydro-2,2,3-trimethyl-1,3,5-triazino[1,2-a]benzimidazole-10-carboxamide The procedure of Example 10 was used to prepare the title compound from 1,2-dihydro-2,2,3-trimethyl-1,3,5-triazino[1,2-a]benzimidazol-4(3H)-one and 4-chlorophenyl isocyanate. The confirmatory elemental analysis for the product, mp 206°–211° C., is shown in Table III.

EXAMPLE 16

N-tert-Butyl-4-oxo-2,3,4,10-tetrahydro-2,2,3-trimethyl-1,3,5-triazino[1,2-a]benzimidazole-10-carboxamide The procedure of Example 10 was used to prepare the title compound from 1,2-dihydro-2,2,3-trimethyl-1,3,5-triazino[1,2-a]benzimidazol-4(3H)-one and tert-butyl isocyanate. The white solid product melted at 209° C. with decomposition. The confirmatory elemental analysis is shown in Table III.

EXAMPLE 17

10-Acetyl-2,10-dihydro-2,2,3-trimethyl-1,3,5-triazino[1,2-a]benzimidazol-4(3H)-one A 250-ml, round-bottomed flask containing a magnetic stirring bar was charged with 2.45 g (0.0106 mole) of 1,2-dihydro-2,2,3-trimethyl-1,3,5-triazino[1,2-a]benzimidazol-4-(3H)-one, 150 ml of acetone and 1.53 ml of triethylamine. Acetyl chloride (0.86 g, 0.0110 mole) was added rapidly via syringe to the resulting solution. The mixture was stirred for two hours at room temperature after which time a white precipitate of triethylammonium hydrochloride was visible. Examination of the reaction mixture by TLC (silica, 80:2:1, $CHCl_3$: $CH_3OH$: $NH_4OH$) showed that only a trace of starting material remained. The mixture was concentrated in vacuo and the resulting solid was taken up in methylene chloride. The resulting solution was washed with water (3 times) brine, dried (MgSO$_4$) and concentrated under reduced pressure to afford 1.5 g (52% yield) of a white solid which was analytically pure, mp 159°–62° C.

Anal. Calcd. for C$_{14}$H$_{16}$N$_4$O$_2$: C, 61.75; H, 5.92; N, 20.58. Found: C, 61.70; H, 5.71; N, 20.55.

Spectral data: nmr (δ, CDCl$_3$) 1.57 (S, 6H, gem. methyls), 2.70 (S, 3H, COCH$_3$), 3.03 (S, 3H, N—CH$_3$), 6.93–7.37 (m, 2H, aromatic H), 7.77–8.07 (m, 1H, C-6 aromatic H), 8.07–8.40 (m, 1H, C-9 aromatic H); ir ($\nu_{max}^{CHCl_3}$) 3000, 1720 (C=O str.), 1600, 1480, 1380, 1350, 1290, 1190, 1150 cm$^{-1}$.

EXAMPLE 18

N-Cyclohexyl-4-oxo-2,3,4,10-tetrahydro-2,2,3-trimethyl-1,3,5-triazino[1,2-a]benzimidazole-10-carboxamide The subject compound was prepared from 1,2-dihydro-2,2,3-trimethyl-1,3,5-triazino[1,2-a]benzimidazol-4(3H)-one and cyclohexyl isocyanate according to the method of Example 10. The confirmatory elemental analysis for the product, mp 114°–116° C., is shown in Table III.

EXAMPLE 19

2,10-Dihydro-2,2,3,10-tetramethyl-1,3,5-triazino[1,2-a]benzimidazol-4(3H)-one

A mixture of 2.0 g (0.0087 mole) 1,2-dihydro-2,2,3-trimethyl-1,3,5-triazino[1,2-a]benzimidazol-4(3H)-one, 1.1 ml (0.0174 mole) methyl iodide, anhydrous potassium carbonate (1 gram) and acetone (100 ml) was heated under reflux, with stirring, overnight. After refluxing had continued 21 hours an additional 1 ml of methyl iodide was added and solids removed from the mixture by suction filtration. The filtrate was evaporated under reduced pressure and the resulting residue dissolved in ethyl acetate, washed with water, then with brine and dried over MgSO$_4$, filtered and solvent stripped off to give 1.8 g of crude product. Purification by high pressure liquid chromatography gave a solid, mp 79°–82° C.

Anal. Calcd. for C$_{13}$H$_{16}$N$_4$O: C, 63.91; H, 6.60; N, 22.94. Found: C, 63.79; H, 6.55; N, 22.71.

Spectral data: nmr (δ, DMSO-d$_6$)1.5(S, 6H, gem. methyls), 3.0 (S, 3H, N—CH$_3$), 3.25 (S, 3H, N—CH$_3$), 6.8–7.2 (m, 3H, aromatic H), 7.55–7.84 (m, 1H, aromatic H); ir ($\nu_{max}^{CHCl_3}$) 2955, 1680 (strong, C=N), 1615, 1485, 1478, 1421, 1380, 1200 cm$^{-1}$.

EXAMPLE 20

2,10-Dihydro-10-(ethoxycarbonyl)-2,2,3-trimethyl-1,3,5-triazino[1,2-a]benzimidazol-4(3H)-one The title compound was prepared from 1,2-dihydro-2,2,3-trimethyl-1,3,5-triazino[1,2-a]benzimidazol-4(3H)-one (2.35 g, 0.0102 molel), ethyl chloroformate (1.1 ml, 0.0102 mole) and triethylamine (1 ml, 0.0102 mole) by reaction in 150 ml of acetone solvent according to the general method of Example 17. The yellowish, crude product was chromatographed on a Waters LC 500 instrument to give 1.62 g of a clear oil which crystallized to a solid, mp 84°–86° C. The confirmatory elemental analysis for the product is shown in Table III.

EXAMPLE 21

N-(3,4-Dichlorophenyl)-4-oxo-2,3,4,10-tetrahydro-2,2,3-trimethyl-1,3,5-triazino[1,2-a]benzimidazole-10-carboxamide The procedure of Example 10 was employed to prepare the title compound from 1,2-dihydro-2,2,3-trimethyl-1,3,5-triazino[1,2-a]benzimidazol-4(3H)-one and 3,4-dichlorophenyl isocyanate. The confirmatory elemental analysis for the product, mp 198°–200° C., is shown in Table III.

EXAMPLE 22

2,10-Dihydro-10-[(2-methyl)propanoyl]-2,2,3-trimethyl-1,3,5-triazino[1,2-a]benzimidazol-4(3H)-one The general procedure of Example 17 was used to prepare the title compound by reaction of 1,2-dihydro-2,2,3-trimethyl-1,3,5-triazino[1,2-a]benzimidazol-4(3H)-one, isobutyryl chloride and triethylamine in acetone solution. The product was isolated as a yellowish oil which crystallized to a solid, mp 99°–102° C. The confirmatory elemental analysis is shown in Table III.

EXAMPLE 23

2,2-Diethyl-N,3-dimethyl-4-oxo-2,3,4,10-tetrahydro-1,3,5-triazino[1,2-a]benzimidazole-10-carboxamide(23A) and
2,2-Diethyl-1,2-dihydro-3-methyl-1,3,5-triazino[1,2-a]benzimidazol-4(3H)-one(23B)

The title compounds were prepared by reaction of 2-aminobenzimidazole, diethyl ketone and methyl isocyanate, employing the procedure of the first paragraph of Example 1. Liquid chromatographic separation of the reaction products give both the 10-carboxamide (23A), mp 114°–125° C., and the decarbamoylated compound (23B), mp 215° C. (dec.). The confirmatory elemental analyses are shown in Table III.

EXAMPLE 24

2,10-Dihydro-10-[(4-tolyl)sulfonyl]-2,2,3-trimethyl-1,3,5-triazino[1,2-a]benzimidazol-4(3H)-one The general procedure of Example 17 was used to prepare the title compound by reaction of 1,2-dihydro-2,2,3-trimethyl-1,3,5-triazino[1,2-a]benzimidazol-4(3H)-one, para-toluenesulfonyl chloride and triethylamine in acetone solution. After recrystallization from ethyl acetate, the product formed colorless prisms, mp 147°–149° C. The confirmatory elemental analytical data are shown in Table III.

EXAMPLE 25

7,8-Dichloro-1,2-dihydro-2,2,3-trimethyl-1,3,5-triazino[1,2-a]benzimidazol-4(3H)-one Reaction of 2-amino-5,6-dichlorobenzimidazole with acetone and methyl isocyanate according to the procedure of Example 1, first paragraph, provided the title compound. In this case, a 10-N-methylcarbamoyl derivative was not isolated from the reaction mixture. The product was recrystallized from acetone to give a solid, mp 220° C. (dec.). The confirmatory elemental analysis is shown in Table III.

EXAMPLE 26

N,3-Dimethyl-4-oxo-2,3,4,10-tetrahydrospiro[1,3,5-triazino[1,2-a]benzimidazole-2,1'-cyclopentane]-10-carboxamide Employing the general procedure of Example 1, paragraph 1,2-aminobenzimidazole (16 g, 0.012 mole), methyl isocyanate (14 ml, 0.024 mole) and cyclopentanone (250 ml) were reacted using 250 ml of tetrahydrofuran as a cosolvent with the excess cyclopentanone. Workup of the reaction mixture by liquid chromatography using $CH_2Cl_2/CH_3OH$ (80/1:V/V) gave the product as a solid, mp 150° C. (dec). The confirmatory elemental analysis is shown in Table III.

EXAMPLE 27

3-Methyl-4-oxo-1,2,3,4-tetrahydrospiro[1,3,5-triazino[1,2-a]benzimidazole-2,1'-cyclopentane]

The reaction product of Example 26 was hydrolyzed by 10% aqueous sodium hydroxide and THF to give the title compound, employing the procedure of Example 1, paragraph 2. The product was recrystallized from acetone to give a solid, mp 180°–182° C. The confirmatory elemental analysis is shown in Table III.

EXAMPLE 28

1,2-Dihydro-2,3-dimethyl-2-(2-methylpropyl)-1,3,5-triazino[1,2-a]benzimidazol-4(3H)-one 2-Aminobenzimidazole, methyl isobutyl ketone and ethyl isocyanate were reacted as in Example 26 using an equal volume of THF as cosolvent with the excess ketone. Working up the reaction mixture gave a crude fraction of the 10-N-methylcarbamoyl derivative of the title compound which was not purified but hydrolyzed by the 10% NaOH-THF procedure of Example 1, paragraph 2. The title compound was obtained as a solid, mp 150°–157° C. The confirmatory elemental analysis is shown in Table III.

EXAMPLE 29

1,2-Dihydro-2,2,3,7,8-pentamethyl-1,3,5-triazino[1,2-a]benzimidazol-4(3H)-one

2-Amino-5,6-dimethylbenzimidazole monohydrate, acetone and methyl isocyanate were reacted, conducting the initial condensation and subsequent base hydrolysis of the intermediate 10-N-methylcarbamoyl precursor as described in Example 1. The title compound was recovered and purified by liquid chromatography to give a solid, mp 211° C. (dec.). The confirmatory elemental analysis is shown in Table III.

EXAMPLE 30

2,10-Dihydro-10-(methylsulfonyl)-2,2,3-trimethyl-1,3,5-triazino[1,2-a]benzimidazol-4(3H)-one The general procedure of Example 17 was employed to prepare the title compound by reaction of 1,2-dihydro-2,2,3-trimethyl-1,3,5-triazino[1,2-a]benzimidazol-4(3H)-one, methanesulfonyl chloride and triethylamine in acetone solution. The title compound was isolated and purified by liquid chromatography giving a solid, mp 147° C. (dec.). The confirmatory elemental analysis is shown in Table III.

EXAMPLE 31

1,2-Dihydro-2,2,3-trimethyl-1,3,5-triazino[1,2-a]benzimidazol-4(3H)-thione

The subject compound was prepared by reacting 2-aminobenzimidazole, acetone and methyl isothiocyanate by the procedure described in the first paragraph of Example 1, above. In this case, a 10-N methylthiocarbamoyl derivative was not obtained and the subject compound was recovered directly from the Soxhlet extraction and recrystallized from acetone to give crystals, mp 186° C. (with decomposition).

Anal. Calcd. for $C_{12}H_{14}N_4S$: C, 58.51; H, 5.73; N, 22.75. Found: C, 58.65; H, 5.62; N, 22.98.

Spectral data: nmr ($\delta$, $CDCl_3$) 1.75 (S, 6H, gem. methyls), 3.53 (S, 3H, N—$CH_3$), 6.90–7.37 (m, 3H, aromatic H), 8.60–9.00 (m, 1H, aromatic H); ir ($\nu_{max}^{CHCl_3}$) 2700–3300 (broad, NH), 1670 (C=N str), 1590, 1491, 1455, 1404, 1365, 1325, 1268, 1232, 1172, 1152, 1138, 1121, 1088, 1043, 1015, 972, 885, 752, 735 cm$^{-1}$; $^{13}$C nmr ($\delta$, $CDCl_3$), 27.0 (gem dimethyls), 34.0 (N—$CH_3$), 73.0

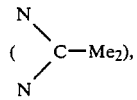

115.5, 117, 121, 124.9 (aromatic carbons bearing H), 132.5, 142.9, 149.5 (carbons without H), 174 (C=S).

EXAMPLE 32

2-Cyclopropyl-1,2-dihydro-2,3-dimethyl-1,3,5-triazino[1,2-a]benzimidazol-4(3H)-one 2-Aminobenzimidazole, cyclopropyl methyl ketone and methyl isocyanate were reacted as in Example 26 using THF as a cosolvent with the excess ketone. Working up the reaction mixture gave none of the expected 10-N-methylcarbamoyl derivative of the title compound but, rather, the title compound itself, recrystallized from acetone to give a solid, mp 200° C. (dec.). The confirmatory elemental analysis is shown in Table III.

EXAMPLE 33

4-Oxo-2,3,4,10-tetrahydro-N,2,2,3-tetramethyl-1,3,5-triazino[1,2-a]benzimidazole-10-carboxamide: Preparation by iminium salt procedure (illustrating Method II, above)

To a stirred solution of 2 g. (0.015 mole) of 2-aminobenzimidazole in 50 ml of acetone was added a solution of 2.99 g (0.015 mole) of N-isopropylidenepyrrolidinium perchlorate[2] in acetone, in one portion, followed by an 8-g portion of 3A molecular sieves. The resulting mixture was heated under reflux with stirring for approximately 23 hours, allowed to cool, 1.71 g (0.03 mole) of methyl isocyanate added via syringe, and the mixture then stirred overnight at room temperature. The reaction mixture was filtered and the filtrate freed of solvent under reduced pressure. The resulting residue was taken up in chloroform, washed with water, dried ($MgSO_4$) and vacuum stripped to give 3.4 g of a dark oil, identified by its proton NMR spectrum as the desired product. The latter was purified on a high-pressure liquid chromatograph, eluting with $CH_2Cl_2/CH_3OH$ (97.6%/2.4% by volume), giving 1.25 g (33% yield) of 4-oxo-2,3,4,10-tetrahydro-N,2,2,3-tetramethyl-1,3,5-triazino[1,2-a]benzimidazole-10-carboxamide.

(2) Prepared by the procedure of N. J. Leonard and J. V. Paukstelis as described in J. Org. Chem. 28, 3021 (1963).

The above compound may be used as a herbicide or, alternatively, may be converted to the herbicidal 1,2-dihydro-2,2,3-trimethyl-1,3,5-triazino[1,2-a]benzimidazol-4(3H)-one as described in Example 1.

TABLE II
Structural Key

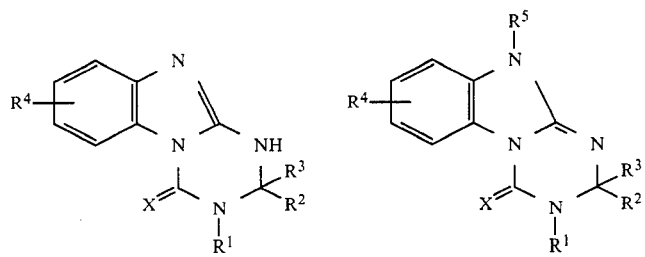

| Example | R¹ | R² | R³ | R⁴ | R⁵ | X |
|---|---|---|---|---|---|---|
| 1(A) | CH₃ | CH₃ | CH₃ | H | CH₃NHCO— | O |
| 1(B) | CH₃ | CH₃ | CH₃ | H | —* | " |
| 2 | C₂H₅ | CH₃ | CH₃ | H | — | " |
| 3 | n-C₃H₇ | CH₃ | CH₃ | H | n-C₃H₇NHCO— | " |
| 4 | n-C₃H₇ | CH₃ | CH₃ | H | — | " |
| 5 | n-C₄H₉ | CH₃ | CH₃ | H | — | " |
| 6 | H | CH₃ | CH₃ | H | — | " |
| 7 | (CH₃)₂CH— | CH₃ | CH₃ | H | (CH₃)₂CHNHCO— | " |
| 8 | CH₃ | CH₃ | C₂H₅ | H | CH₃NHCO— | " |
| 9 | CH₃ | CH₃ | C₂H₅ | H | — | " |
| 10 | n-C₄H₉ | CH₃ | CH₃ | H | CH₃NHCO— | " |
| 11 | CH₃ | CH₃ | CH₃ | H | C₂H₅NHCO— | " |
| 12 | CH₃ | CH₃ | CH₃ | H | (CH₃)₂CHNHCO— | " |
| 13 | CH₃ | CH₃ | CH₃ | H | n-C₃H₇NHCO— | " |
| 14 | CH₃ | CH₃ | CH₃ | H | n-C₄H₉NHCO— | " |
| 15 | CH₃ | CH₃ | CH₃ | H | Cl—⟨C₆H₄⟩—NHCO— | " |
| 16 | CH₃ | CH₃ | CH₃ | H | (CH₃)₃CNHCO— | " |
| 17 | CH₃ | CH₃ | CH₃ | H | CH₃CO— | " |
| 18 | CH₃ | CH₃ | CH₃ | H | ⟨S⟩—NHCO— | " |
| 19 | CH₃ | CH₃ | CH₃ | H | CH₃ | " |
| 20 | CH₃ | CH₃ | CH₃ | H | C₂H₅OCO— | " |
| 21 | CH₃ | CH₃ | CH₃ | H | Cl,Cl—⟨C₆H₃⟩—NHCO— | " |
| 22 | CH₃ | CH₃ | CH₃ | H | (CH₃)₂CHCO— | " |
| 23(A) | CH₃ | C₂H₅ | C₂H₅ | H | CH₃NHCO— | " |
| 23(B) | CH₃ | C₂H₅ | C₂H₅ | H | — | " |
| 24 | CH₃ | CH₃ | CH₃ | H | CH₃—⟨C₆H₄⟩—SO₂— | " |
| 25 | CH₃ | CH₃ | CH₃ | 7,8-Cl₂ | — | " |
| 26 | CH₃ | —(CH₂)₄— | | H | CH₃NHCO— | " |
| 27 | CH₃ | —(CH₂)₄— | | H | — | " |
| 28 | CH₃ | CH₃ | —CH₂CH(CH₃)₂ | H | — | " |
| 29 | CH₃ | CH₃ | CH₃ | 7,8-(CH₃)₂ | — | " |
| 30 | CH₃ | CH₃ | CH₃ | H | CH₃SO₂— | " |
| 31 | CH₃ | CH₃ | CH₃ | H | — | S |
| 32 | CH₃ | CH₃ | ▷— | H | — | O |

*— designates hydrogen

TABLE III

Physical Properties and Elemental Analyses

| Compound Example No. | mp °C. | Molec. Form. | Calcd. C | Calcd. H | Calcd. N | Found C | Found H | Found N |
|---|---|---|---|---|---|---|---|---|
| 1B | 209 dec | $C_{12}H_{14}N_4O$ | 62.59 | 6.13 | 24.33 | 62.47 | 6.16 | 24.24 |
| 2 | >300 dec | $C_{13}H_{16}N_4O$ | 63.91 | 6.60 | 22.93 | 63.81 | 6.74 | 22.91 |
| 3 | 72–74 | $C_{18}H_{25}N_5O_2$ | 62.9 | 7.3 | 20.3 | 63.09 | 7.00 | 20.21 |
| 4 | 170 dec | $C_{14}H_{18}N_4O$ | 65.1 | 7.0 | 21.7 | 65.04 | 6.94 | 21.72 |
| 5 | 142–49 dec | $C_{15}H_{20}N_4O$ | 66.1 | 7.4 | 20.6 | 64.98 | 7.99 | 19.66 |
| 6 | 178–80 dec | $C_{11}H_{12}N_4O$ | 61.09 | 5.60 | 25.91 | 61.00 | 5.49 | 25.38 |
| 7 | 80–89 | $C_{18}H_{25}N_5O_2$ | 62.9 | 7.3 | 20.4 | 63.19 | 7.41 | 19.67 |
| 8 | 113–19 dec | $C_{15}H_{19}N_5O_2$ | 59.78 | 6.35 | 23.24 | 59.38 | 6.16 | 23.41 |
| 9 | 202 dec | $C_{13}H_{16}N_4O$ | 63.91 | 6.60 | 22.94 | 63.64 | 6.54 | 23.08 |
| 1A | 164 dec | $C_{14}H_{17}N_5O_2$ | 58.52 | 5.97 | 24.38 | 58.60 | 5.91 | 24.04 |
| 10 | 124–29 | $C_{17}H_{23}N_5O_2$ | 61.99 | 7.04 | 21.26 | 62.11 | 7.04 | 21.15 |
| 11 | 127–31 | $C_{15}H_{19}N_5O_2$ | 59.78 | 6.35 | 23.24 | 59.82 | 6.39 | 23.43 |
| 12 | 85–87 | $C_{16}H_{21}N_5O_2$ | 60.93 | 6.71 | 22.21 | 60.69 | 6.85 | 22.36 |
| 13 | 93–96 | $C_{16}H_{21}N_5O_2$ | 60.93 | 6.71 | 22.21 | 60.67 | 6.56 | 22.08 |
| 14 | 95–97 | $C_{17}H_{23}N_5O_2$ | 61.98 | 7.04 | 21.26 | 61.84 | 7.11 | 21.02 |
| 15 | 206–11 dec | $C_{19}H_{18}ClN_5O_2$ | 59.45 | 4.73 | 18.25 | 58.86 | 4.66 | 17.93 |
| 16 | 209 dec | $C_{17}H_{23}N_5O_2$ | 61.98 | 7.04 | 21.26 | 61.94 | 7.02 | 21.25 |
| 17 | 159–62 | $C_{14}H_{16}N_4O_2$ | 61.75 | 5.92 | 20.58 | 61.70 | 5.71 | 20.55 |
| 18 | 114–16 | $C_{19}H_{25}N_5O_2$ | 64.20 | 7.09 | 19.71 | 64.19 | 6.86 | 19.57 |
| 19 | 79–82 | $C_{13}H_{16}N_4O$ | 63.91 | 6.60 | 22.94 | 63.79 | 6.55 | 22.71 |
| 29 | 211 dec | $C_{14}H_{18}N_4O$ | 65.09 | 7.02 | 21.69 | 65.21 | 6.91 | 21.72 |
| 20 | 84–86 | $C_{15}H_{18}N_4O_3$ | 59.59 | 6.00 | 18.53 | 59.40 | 5.93 | 18.90 |
| 21 | 198–200 | $C_{19}H_{17}Cl_2N_5O_2$ | 54.55 | 4.10 | 16.74 | 54.37 | 4.02 | 16.74 |
| 22 | 99–102 | $C_{16}H_{20}N_4O_2$ | 63.98 | 6.71 | 18.65 | 63.79 | 6.67 | 18.66 |
| 23A | 114–25 | $C_{16}H_{21}N_5O_2$ | 60.93 | 6.71 | 22.21 | 60.81 | 6.62 | 21.84 |
| 23B | 215 dec | $C_{14}H_{18}N_4O$ | 65.09 | 7.02 | 21.69 | 65.04 | 6.96 | 21.93 |
| 26 | 150 dec | $C_{16}H_{19}N_5O_2$ | 61.32 | 6.11 | 22.35 | 61.28 | 6.11 | 22.11 |
| 27 | 180–82 | $C_{14}H_{16}N_4O$ | 65.60 | 6.29 | 21.86 | 65.67 | 6.25 | 21.89 |
| 28 | 150–57 | $C_{15}H_{20}N_4O$ | 66.15 | 7.40 | 20.57 | 65.80 | 7.33 | 20.38 |
| 30 | 147 dec | $C_{13}H_{16}N_4O_3S$ | 50.63 | 5.23 | 18.17 | 49.87 | 5.16 | 17.93 |
| 31 | 186 dec | $C_{12}H_{14}N_4S$ | 58.51 | 5.73 | 22.75 | 58.65 | 5.64 | 22.98 |
| 32 | 200 dec | $C_{14}H_{16}N_4O$ | 65.62 | 6.29 | 21.86 | 65.35 | 6.21 | 21.67 |
| 25 | 220 dec | $C_{12}H_{12}Cl_2N_4O$ | 48.17 | 4.04 | 18.73 | 48.08 | 3.88 | 19.13 |
| 24 | 147–149 | $C_{19}H_{20}N_4O_3S$ | 59.36 | 5.24 | 14.57 | 59.22 | 5.21 | 14.53 |

Our compounds possess activity both as pre-emergence and post-emergence herbicides and, accordingly, one aspect of this invention comprises the application of the operative materials to undesired vegetation by any means whereby said materials are brought into contact with living plants (which include seed and germinating seedlings), e.g., by application to the soil before any plants emerge or by direct application to foliage.

The compounds are effective for both grassy weeds such as crabgrass, wild oats, barnyard grass, yellow foxtail, green foxtail, quackgrass, and rye grass, and broadleaf weeds such as mustard, pigweed, lambsquarters, and sheep sorrel are readily controlled while a broad spectrum of crops is unaffected. Illustrative of tolerant crops are cotton, soybeans, peanuts, beans, peas, onions, alfalfa, red clover, lespediza, field corn and the like.

Our new toxicants may be applied conveniently in the form of a spray containing the active ingredient in a concentration within the range of 0.01–20.0% by weight, and preferably from 1 to 10.0% by weight. Thorough coverage of the foliage is effected for contact killing. For pre-emergence control of plants amounts within the range of 1/16 to 100 pounds per acre are generally used.

The compounds may be dispersed directly in water or a solution in an organic solvent, such as acetone, dimethylformamide, and dimethylsulfoxide emulsified in aqueous medium by the aid of a dispersing agent. As dispersing and wetting agents there may be employed soft or hard sodium or potassium soaps, alkylated aromatic sodium sulfonates such as sodium dodecylbenzenesulfonate, an amine salt as for example dibutylammonium dodecylbenzenesulfonate, alkali metal salts of sulfated fatty alcohols, ethylene oxide condensation products of alkyl phenols, or tall oil or higher mercaptans and other dispersing and wetting agents. Formulation of dry compositions is accomplished by mixing with finely divided solid carriers. Suitable carriers comprise talc, clay, pyrophyllite, silica and fuller's earth. Usually the toxicant will be only a minor proportion. The dry formulation may be used as a dust or dispersed in aqueous medium before application. If the latter it is convenient to incorporate a wetting or dispersing aid into the formulation.

Both the solid and the liquid formulations above described are useful in the application of herbicides because they facilitate uniform distribution and aid in the destruction of undesirable plants by maintaining the active ingredient in a form which enables prompt assimilation by the plant and efficient utilization of its weed destroying properties. The described conditioning agents enable the proper use by an unskilled operator without elaborate equipment to achieve the desired herbicidal effects.

The effectiveness of compounds representative of this invention as terrestrial herbicides were evaluated as pre-emergence herbicides and post-emergence herbicides. The test plants were mustard, teaweed, crabgrass and giant foxtail. For the pre-emergence test, seeds of the type of plants as shown in Table IV were sown in fresh soil. In the pre-emergence test, the soil was sprayed with a solution of the test compound immediately after the seeds were planted. The solution was about a 1% by weight solution of the test compound in acetone. The compounds were applied at the rate of 8 lbs/acre of soil surface, except where otherwise indicated in Table IV.

Approximately three weeks after spray applications, the herbicidal activity of the compound was determined by visual observation of the treated areas in comparison with untreated controls. These observations are reported in Table IV on a scale of 0 to 10, wherein 0=no effect and 10 equals 100% control of plant growth. In addition the herbicidal affects were noted with respect to growth inhibition (G), burn (B), necrosis (N), emergence reduction (E) and chlorosis (C).

In the post-emergence test the soil and developing plants were sprayed about two weeks after the seeds were sown. Except where indicated otherwise in Table IV, the compounds were applied at the rate of 8 lbs/acre from about a 1% by weight solution of the test compound in acetone. The post emergence herbicidal activity was measured in the same way as the pre-emergence activity at three weeks following treatment.

The results are indicated in Table IV.

TABLE IV

| Compound/Example No. | Herbicidal Activity[3][4] | | | | | | | |
|---|---|---|---|---|---|---|---|---|
| | Test Plant | | | | | | | |
| | Mustard | | Teaweed | | Crabgrass | | Giant Foxtail | |
| | Post | Pre | Post | Pre | Post | Pre | Post | Pre |
| 1B[5] | 10B | 10N | 10B | 10N | 10B | 10N | 3N | 4B |
| 2 | 10N | 10N | 10N | 10N | 10N | 10N | 9N | 10N |
| 3 | 10B | 10N | 10G | 10N | 8B | 10N | 9B | 10N |
| 4 | 10N | 10E | 10G | 10N | 8N | 10E | 4N | 9N |
| 5 | 10N | 9G | 0 | 9G | 2G | 9G | 0 | 8N |
| 6 | 10N | 10N | 10N | 10N | 10N | 10N | 10N | 10N |
| 7 | 10N | 10N | 10G | 10N | 5N | 10N | 2G | 2G |
| 8 | 10B | 10N | 10B | 10N | 10B | 10N | 10B | 10N |
| 9 | 10N | 10N | 10G | 10N | 10N | 10N | 10N | 10N |
| 1A | 10B | 10N | 10G | 10N | 10B | 10N | 10B | 10N |
| 10 | 10N | 10E | 10G | 0 | 10G | 6G | 3G | 0 |
| 11 | 10B | 10N | 10B | 10N | 10B | 8N | 10B | 10N |
| 13 | 10B | 10N | 10B | 10N | 10B | 9N | 10B | 10N |
| 12 | 10B | 10N | 10B | 10N | 10B | 10N | 10B | 10N |
| 14 | 10B | 10N | 10B | 10N | 10B | 10N | 10B | — |
| 15 | 10B | 0 | 10B | 0 | 10B | 0 | 10B | 0 |
| 16 | 10B | 10N | 10B | 10N | 10B | 10N | 10B | 10N |
| 17 | 10B | 10N | 10B | 10N | 10B | 10N | 10B | 0 |
| 18 | 10B | 10N | 10B | 10N | 10B | 10N | 10B | 10N |
| 19 | 10B | 8G | 10G | 10E | 10B | 4G | 10B | 5G |
| 29 | 8N | 2N | 10N | 3E | 5N | 7G | 0 | 0 |
| 20 | 10B | 10N | 10B | 10N | 10B | 10N | 10B | 9N |
| 21 | 10N | 9G | 10N | 7G | 10N | 0 | 10N | 0 |
| 22 | 10B | 10N | 10B | 10N | 10B | 10N | 10B | 9G |
| 23A | 10N | 7N | 10N | 10N | 10N | 10N | 10N | 8G |
| 23B | 8N | 10N | 10G | 7G | 6G | 10N | 0 | 3G |
| 26 | 8G | 3G | 0 | 0 | 3G | 2G | 0 | 0 |
| 27 | 10N | 9G | 0 | 0 | 5N | 0 | 0 | 0 |
| 28 | 10N | 9G | 10G | 5G | 10N | 0 | 5N | 0 |
| 30 | 10N | 10N | 10G | 10N | 10N | 10N | 10N | 10N |
| 31 | 10N | 5G | 10N | 2G | 10N | 10E | 0 | 0 |
| 32 | 10N | 10N | 10N | 10N | 10N | 10N | 10N | 2G |
| 25 | 10N | 4G | 10N | 0 | 0 | 4G | 0 | 0 |
| 24 | 10N | 10N | 10N | 10N | 10N | 10N | 10N | 2G |

[3]On a scale of 0-10 wherein 0 = no effect and 10 = 100% response; Post = postemergent application; Pre = preemergent application; N = necrosis; G = growth inhibition, B = burn, E = emergence reduction, C = chlorosis
[4]Except where indicated otherwise rates were 8 lbs./acre.
[5]Rate 2 lbs./acre.

What is claimed is:

1. Compounds selected from the group consisting of compounds having the general formula:

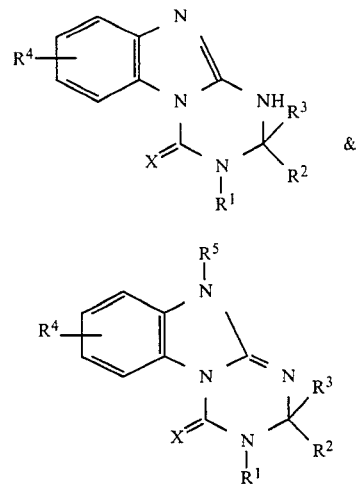

wherein
$R^1$ is hydrogen, lower alkyl ($C_1$–$C_6$), cycloalkyl ($C_3$–$C_7$) lower alkenyl ($C_2$–$C_6$), lower alkynyl ($C_3$–$C_6$), haloalkyl ($C_1$–$C_6$) and alkoxyalkyl ($C_2$–$C_6$);

$R^2$ and $R^3$ individually are hydrogen, ketoalkyl ($C_3$–$C_5$), lower alkyl ($C_1$–$C_6$), cycloalkyl ($C_3$–$C_6$), alkoxyalkyl ($C_2$–$C_4$), alkenyl ($C_2$–$C_6$), haloalkyl ($C_1$–$C_6$), and acyl ($C_2$–$C_4$); $R^2$ and $R^3$ taken together can also form a spirocyclic ring of $C_3$–$C_5$ carbon atoms;

$R^4$ individually can be H, alkyl ($C_1$–$C_6$), a maximum of two halogens selected from the group consisting of Cl, F, and Br, alkoxyl ($C_1$–$C_4$), nitro, alkylthio ($C_1$–$C_4$) and alkylsulfonyl ($C_1$–$C_4$);

$R^5$ may be hydrogen, carbamoyl, N-alkylcarbamoyl ($C_2$–$C_{14}$), N-arylcarbamoyl, N-(substituted aryl)-carbamoyl, N-haloalkylcarbamoyl ($C_2$–$C_{12}$), N-carboalkoxyalkylcarbamoyl, N-carboxyalkylcarbamoyl ($C_3$–$C_{14}$), N-alkoxyalkylcarbamoyl ($C_3$–$C_{14}$), N-arylsulfonylcarbamoyl, acyl($C_1$–$C_{14}$), aroyl, substituted aroyl, alkoxycarbonyl ($C_2$–$C_{14}$), aryloxycarbonyl, hydroxyacyl ($C_2$–$C_8$), alkoxyacyl ($C_3$–$C_9$) alkylthioacyl ($C_3$–$C_9$), alkylsulfonylacyl ($C_3$–$C_7$), N,N-dialkylaminoacyl ($C_4$–$C_{10}$), alkylsulfonyl ($C_3$–$C_{14}$), haloalkylsulfonyl ($C_1$–$C_{14}$), arylsulfonyl, substituted arylsulfonyl, alkyl ($C_1$–$C_{14}$), hydroxyalkyl ($C_1$–$C_8$), alkoxyalkyl ($C_2$–$C_9$), haloalkyl ($C_1$–$C_8$), cycloalkyl ($C_3$–$C_7$), alkenyl ($C_2$–$C_{14}$), cycloalkenyl ($C_5$–$C_7$), alkynyl ($C_2$–$C_{14}$), aryl and substituted aryl;

X is oxygen or sulfur.

2. A compound according to claim 1 wherein $R^1$ is alkyl containing 1-4 carbon atoms.

3. A compound according to claim 1 wherein $R^1$ is methyl.

4. A compound according to claim 1 wherein $R^2$ and $R^3$ individually are alkyl containing 1-3 carbon atoms and cycloalkyl containing 3-5 carbon atoms.

5. A compound according to claim 1 wherein $R^4$ is alkyl containing 1-4 carbon atoms.

6. A compound according to claim 1 wherein $R^4$ is hydrogen.

7. A compound according to claim 1 wherein $R^5$ is hydrogen, N-alkylcarbamoyl ($C_2$–$C_{14}$), N-arylcarbamoyl, N-(substituted aryl)carbamoyl, acyl($C_1$–$C_{14}$), alkoxycarbonyl (C$_2$–C$_{14}$), alkylsulfonyl (C$_1$–C$_{14}$), arylsulfonyl and substituted arylsulfonyl.

8. Compounds selected from the group consisting of compounds having the general formula:

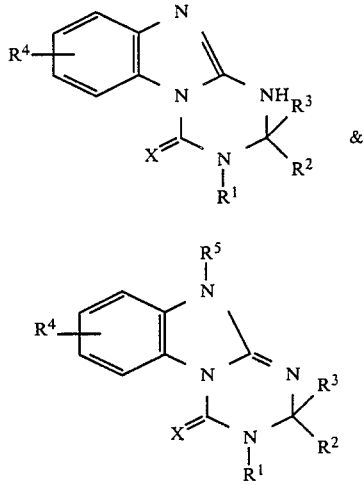

wherein

X is oxygen or sulfur

R$^1$ is hydrogen, lower alkyl (C$_1$–C$_6$), cycloalkyl (C$_3$–C$_7$) lower alkenyl (C$_2$–C$_6$), lower alkynyl (C$_3$–C$_6$), haloalkyl (C$_1$–C$_6$) and alkoxyalkyl (C$_2$–C$_6$);

R$^2$ and R$^3$ individually are alkyl containing 1–3 carbon atoms and cycloalkyl containing 3–5 carbon atoms, R$^4$ is H or alkyl containing 1–4 carbon atoms, and R$^5$ is hydrogen, carbamoyl, N-alkylcarbamoyl (C$_2$–C$_{14}$), N-arylcarbamoyl, N-(substituted aryl)carbamoyl, N-haloalkylcarbamoyl (C$_2$–C$_{12}$), N-carboalkoxyalkylcarbamoyl, N-carboxyalkylcarbamoyl (C$_3$–C$_{14}$), N-alkoxyalkylcarbamoyl (C$_3$–C$_{14}$), N-arylsulfonylcarbamoyl, acyl(C$_1$–C$_{14}$), aroyl, substituted aroyl, alkoxycarbonyl (C$_2$–C$_{14}$), aryloxycarbonyl, hydroxyacyl (C$_2$–C$_8$), alkoxyacyl (C$_3$–C$_9$), alkylthioacyl (C$_3$–C$_9$), alkylsulfonylacyl (C$_3$–C$_7$), N,N-dialkylaminoacyl (C$_4$–C$_{10}$), alkylsulfonyl (C$_1$–C$_{14}$), haloalkylsulfonyl (C$_1$–C$_{14}$), arylsulfonyl, substituted arylsulfonyl, alkyl (C$_1$–C$_{14}$), hydroxyalkyl (C$_1$–C$_8$), alkoxyalkyl (C$_2$–C$_9$), haloalkyl (C$_1$–C$_8$), cycloalkyl (C$_3$–C$_7$), alkenyl (C$_2$–C$_{14}$), cycloalkenyl (C$_5$–C$_7$), alkynyl (C$_2$–C$_{14}$), aryl and substituted aryl.

9. A compound according to claim 8 wherein R$^1$ is alkyl containing 1–4 carbon atoms.

10. A compound according to claim 9 wherein R$^1$ is methyl.

11. A compound according to claim 9 wherein R$^5$ is hydrogen, N-alkylcarbamoyl (C$_2$–C$_{14}$), N-arylcarbamoyl, N-(substituted aryl)carbamoyl, acyl(C$_1$–C$_{14}$), alkoxycarbonyl (C$_2$–C$_{14}$), alkylsulfonyl (C$_1$–C$_{14}$), arylsulfonyl and substituted arylsulfonyl.

12. Compounds selected from the group consisting of compounds having the general formula:

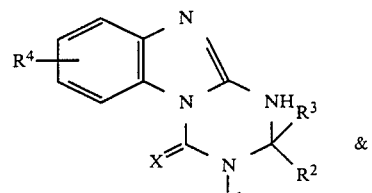

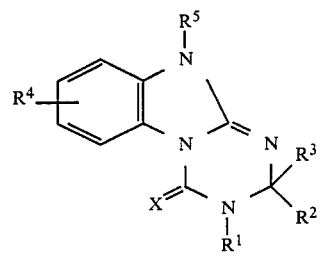

wherein

R$^1$ is alkyl containing 1–4 carbon atoms,

R$^2$ and R$^3$ individually are alkyl containing 1–3 carbon atoms and cycloalkyl containing 3–5 carbon atoms, R$^4$ is H or alkyl containing 1–4 carbon atoms, and R$^5$ is hydrogen, N-alkylcarbamoyl (C$_2$–C$_{14}$), N-arylcarbamoyl, N-(substituted aryl)carbamoyl, acyl (C$_1$–C$_{14}$), alkoxycarbonyl (C$_2$–C$_{14}$), alkylsulfonyl (C$_1$–C$_{14}$), arylsulfonyl and substituted arylsulfonyl.

13. A compound according to claim 12 wherein R$^1$ is methyl.

14. A compound according to claim 12 wherein R$^4$ is hydrogen.

15. 1,2-Dihydro-2,2,3-trimethyl-1,3,5-triazino[1,2-a]benzimidazol-4(3H)-one.

16. 1,2-Dihydro-2,3-dimethyl-2-ethyl-1,3,5-triazino[1,2-a]benzimidazol-4(3H)-one.

17. 4-Oxo-2,3,4,10-tetrahydro-N-2,2,3-tetramethyl-1,3,5-triazino[1,2-a]benzimidazole-10-carboxamide.

18. 2-Ethyl-4-oxo-2,3,4,10-tetrahydro-N,2,3-trimethyl-1,3,5-triazino[1,2-a]benzimidazole-10-carboxamide.

19. 2,10-Dihydro-10-(methylsulfonyl)-2,2,3-trimethyl-1,3,5-triazino[1,2-a]benzimidazol-4(3H)-one.

20. 2,10-Dihydro-10-[(4-tolyl)sulfonyl]-2,2,3-trimethyl-1,3,5-triazino[1,2-a]benzimidazol-4(3H)-one.

21. A terrestrial herbicidal composition comprising a terrestrial herbicidally acceptable carrier and, as an active toxicant, herbicidally effective amounts of a compound selected from the group consisting of compounds having the general formula:

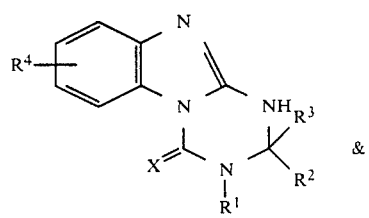

-continued

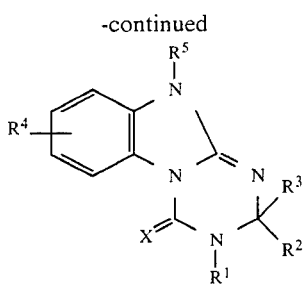

wherein
- $R^1$ is hydrogen, lower alkyl ($C_1$–$C_6$), cycloalkyl ($C_3$–$C_7$) lower alkenyl ($C_2$–$C_6$), lower alkynyl ($C_3$–$C_6$), haloalkyl ($C_1$–$C_6$ and alkoxyalkyl ($C_2$–$C_6$);
- $R^2$ and $R^3$ individually are hydrogen, ketoalkyl ($C_3$–$C_5$), lower alkyl ($C_1$–$C_6$), cycloalkyl ($C_3$–$C_6$), alkoxyalkyl ($C_2$–$C_4$), alkenyl ($C_2$–$C_6$), haloalkyl ($C_1$–$C_6$), and acyl ($C_2$–$C_4$); $R^2$ and $R^3$ taken together can also form a spirocyclic ring of $C_3$–$C_5$ carbon atoms;
- $R^4$ individually can be H, alkyl ($C_1$–$C_6$), a maximum of two halogens selected from the group consisting of Cl, F, and Br, alkoxyl ($C_1$–$C_4$), nitro, alkylthio ($C_1$–$C_4$) and alkylsulfonyl ($C_1$–$C_4$);
- $R^5$ may be hydrogen, carbamoyl, N-alkylcarbamoyl ($C_2$–$C_{14}$), N-arylcarbamoyl, N-(substituted aryl)-carbamoyl, N-haloalkylcarbamoyl ($C_2$–$C_{12}$), N-carboalkoxyalkylcarbamoyl, N-carboxyalkylcarbamoyl ($C_3$–$C_{14}$), N-alkoxyalkylcarbamoyl ($C_3$–$C_{14}$), N-arylsulfonylcarbamoyl, acyl($C_1$–$C_{14}$), aroyl, substituted aroyl, alkoxycarbonyl ($C_2$–$C_{14}$), aryloxycarbonyl, hydroxyacyl ($C_2$–$C_8$), alkoxyacyl ($C_3$–$C_9$), alkylthioacyl ($C_3$–$C_9$), alkylsulfonylacyl ($C_3$–$C_7$), N,N-dialkylaminoacyl ($C_4$–$C_{10}$), alkylsulfonyl ($C_1$–$C_{14}$), haloalkylsulfonyl ($C_1$–$C_{14}$), arylsulfonyl, substituted arylsulfonyl, alkyl ($C_1$–$C_{14}$), hydroxyalkyl ($C_1$–$C_8$), alkoxyalkyl ($C_2$–$C_9$), haloalkyl ($C_1$–$C_8$), cycloalkyl ($C_3$–$C_7$), alkenyl ($C_2$–$C_{14}$), cycloalkenyl ($C_5$–$C_7$), alkynyl ($C_2$–$C_{14}$), aryl and substituted aryl;
- X is oxygen or sulfur.

22. A terrestrial herbicidal composition according to claim 21 wherein $R^1$ is alkyl containing 1–4 carbon atoms.

23. A terrestrial herbicidal composition according to claim 21 wherein $R^1$ is methyl.

24. A terrestrial herbicidal composition according to claim 21 wherein $R^2$ and $R^3$ individually are alkyl containing 1–3 carbon atoms and cycloalkyl containing 3–5 carbon atoms.

25. A terrestrial herbicidal composition according to claim 21 wherein $R^4$ is alkyl containing 1–4 carbon atoms.

26. A terrestrial herbicidal composition according to claim 21 wherein $R^4$ is hydrogen.

27. A terrestrial herbicidal composition according to claim 21 wherein $R^5$ is hydrogen, N-alkylcarbamoyl ($C_2$–$C_{14}$), N-arylcarbamoyl, N-(substituted aryl)carbamoyl, acyl($C_1$–$C_{14}$), alkoxycarbonyl ($C_2$–$C_{14}$), alkylsulfonyl ($C_1$–$C_{14}$), arylsulfonyl and substituted arylsulfonyl.

28. A terrestrial herbicidal composition comprising a terrestrial herbicidally acceptable carrier and, as an active toxicant, herbicidally effective amounts of a compound selected from the group consisting of compounds having the general formula:

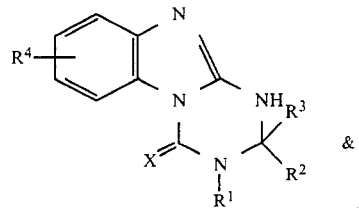

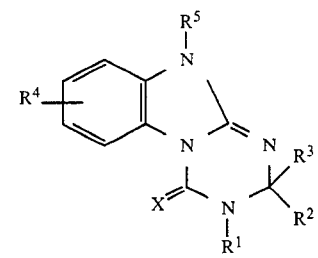

wherein
- $R^1$ is hydrogen, lower alkyl ($C_1$–$C_6$), cycloalkyl ($C_3$–$C_7$) lower alkenyl ($C_2$–$C_6$), lower alkynyl ($C_3$–$C_6$), haloalkyl ($C_1$–$C_6$) and alkoxyalkyl ($C_2$–$C_6$);
- $R^2$ and $R^3$ individually are alkyl containing 1–3 carbon atoms and cycloalkyl containing 3–5 carbon atoms,
- $R^4$ is H, alkyl containing 1–4 carbon atoms, and
- $R^5$ is hydrogen, carbamoyl, N-alkylcarbamoyl ($C_2$–$C_{14}$), N-arylcarbamoyl, N-(substituted aryl)-carbamoyl, N-haloalkylcarbamoyl ($C_2$–$C_{12}$), N-carboalkoxyalkylcarbamoyl, N-carboxyalkylcarbamoyl ($C_3$–$C_{14}$), N-alkoxyalkylcarbamoyl ($C_3$–$C_{14}$), N-arylsulfonylcarbamoyl, acyl($C_1$–$C_{14}$), aroyl, substituted aroyl, alkoxycarbonyl ($C_2$–$C_{14}$), aryloxycarbonyl, hydroxyacyl ($C_2$–$C_8$), alkoxyacyl ($C_3$–$C_9$), alkylthioacyl ($C_3$–$C_9$), alkylsulfonylacyl ($C_3$–$C_7$), N,N-dialkylaminoacyl ($C_4$–$C_{10}$), alkylsulfonyl ($C_1$–$C_{14}$), haloalkylsulfonyl ($C_1$–$C_{14}$), arylsulfonyl, substituted arylsulfonyl, alkyl ($C_1$–$C_{14}$), hydroxyalkyl ($C_1$–$C_8$), alkoxyalkyl ($C_2$–$C_9$), haloalkyl ($C_1$–$C_8$), cycloalkyl ($C_3$–$C_7$), alkenyl ($C_2$–$C_{14}$), cycloalkenyl ($C_5$–$C_7$), alkynyl ($C_2$–$C_{14}$), aryl and substituted aryl.

29. A terrestrial herbicidal composition according to claim 28 wherein $R^1$ is alkyl containing 1–4 carbon atoms.

30. A terrestrial herbicidal composition according to claim 28 wherein $R^1$ is methyl.

31. A terrestrial herbicidal composition according to claim 28 wherein $R^5$ is hydrogen, N-alkylcarbamoyl ($C_2$–$C_{14}$), N-arylcarbamoyl, N-(substituted aryl)carbamoyl, acyl ($C_1$–$C_{14}$), alkoxycarbonyl ($C_2$–$C_{14}$), alkylsulfonyl ($C_1$–$C_{14}$), arylsulfonyl and substituted arylsulfonyl.

32. A method of inhibiting undesired vegetation which comprises applying thereto, in herbicidally effective amounts, a compound selected from the group consisting of compounds having-the following generic formula:

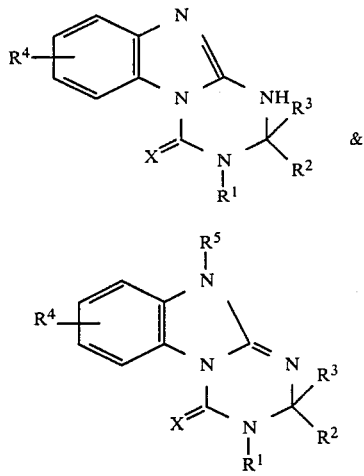

&

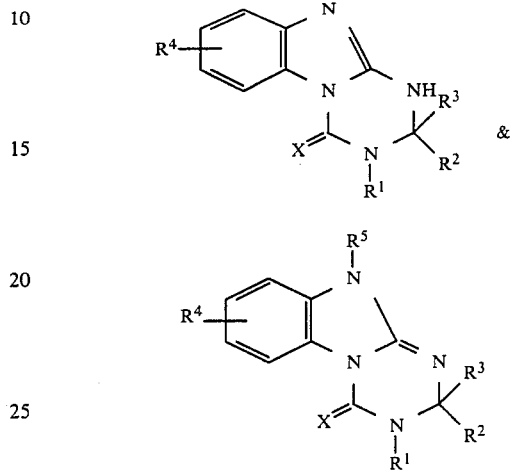

wherein
R$^1$ is hydrogen, lower alkyl (C$_1$-C$_6$), cycloalkyl (C$_3$-C$_7$) lower alkenyl (C$_2$-C$_6$), lower alkynyl (C$_3$-C$_6$), haloalkyl (C$_1$-C$_6$) and alkoxyalkyl (C$_2$-C$_6$);

R$^2$ and R$^3$ individually are hydrogen, ketoalkyl (C$_3$-C$_5$), lower alkyl (C$_1$-C$_6$), cycloalkyl (C$_3$-C$_6$), alkoxyalkyl (C$_2$-C$_4$), alkenyl (C$_2$-C$_6$), haloalkyl (C$_1$-C$_6$), and acyl (C$_2$-C$_4$); R$^2$ and R$^3$ taken together can also form a spirocyclic ring of C$_3$-C$_5$ carbon atoms;

R$^4$ individually can be H, alkyl (C$_1$-C$_6$), a maximum of two halogens selected from the group consisting of Cl, F, and Br, alkoxy (C$_1$-C$_4$), nitro, alkylthio (C$_1$-C$_4$) and alkylsulfonyl (C$_1$-C$_4$);

R$^5$ may be hydrogen, carbamoyl, N-alkylcarbamoyl (C$_2$-C$_{14}$), N-arylcarbamoyl, N-(substituted aryl)carbamoyl, N-haloalkylcarbamoyl (C$_2$-C$_{12}$), N-carboalkoxyalkylcarbamoyl, N-carboxyalkylcarbamoyl (C$_3$-C$_{14}$), N-alkoxyalkylcarbamoyl (C$_3$-C$_{14}$), N-arylsulfonylcarbamoyl, acyl(C$_1$-C$_{14}$), aroyl, substituted aroyl, alkoxycarbonyl (C$_2$-C$_{14}$), aryloxycarbonyl, hydroxyacyl (C$_2$-C$_8$), alkoxyacyl (C$_3$-C$_9$), alkylthioacyl (C$_3$-C$_9$), alkylsulfonylacyl (C$_3$-C$_7$), N,N-dialkylaminoacyl (C$_4$-C$_{10}$), alkylsulfonyl (C$_1$-C$_{14}$), haloalkylsulfonyl (C$_1$-C$_{14}$), arylsulfonyl, substituted arylsulfonyl, alkyl (C$_1$-C$_{14}$), hydroxyalkyl (C$_1$-C$_8$), alkoxyalkyl (C$_2$-C$_9$), haloalkyl (C$_1$-C$_8$), cycloalkyl (C$_3$-C$_7$), alkenyl (C$_2$-C$_{14}$), cycloalkenyl (C$_5$-C$_7$), alkynyl (C$_2$-C$_{14}$), aryl and substituted aryl;

X is oxygen or sulfur.

33. A method according to claim 32 wherein R$^1$ is alkyl containing 1-4 carbon atoms.

34. A compound according to claim 32 wherein R$^1$ is methyl.

35. A compound according to claim 32 wherein R$^2$ and R$^3$ individually are alkyl containing 1-3 carbon atoms and cycloalkyl containing 3-5 carbon atoms.

36. A compound according to claim 32 wherein R$^4$ is alkyl containing 1-4 carbon atoms.

37. A compound according to claim 32 wherein R$^4$ is hydrogen.

38. A compound according to claim 32 wherein R$^5$ is hydrogen, N-alkylcarbamoyl (C$_2$-C$_{14}$), N-arylcarbamoyl, N-(substituted aryl)carbamoyl, acyl(C$_1$-C$_{14}$), alkoxycarbonyl (C$_2$-C$_{14}$), alkylsulfonyl (C$_1$-C$_{14}$), arylsulfonyl and substituted arylsulfonyl.

39. A method of inhibiting undesired vegetation which comprises applying thereto, in herbicidally effective amounts, a compound selected from the group consisting of compounds having the following generic formula:

wherein
R$^1$ is hydrogen, lower alkyl (C$_1$-C$_6$), cycloalkyl (C$_3$-C$_7$) lower alkenyl (C$_2$-C$_6$), lower alkynyl (C$_3$-C$_6$), haloalkyl (C$_1$-C$_6$) and alkoxyalkyl (C$_2$-C$_6$);

R$^2$ and R$^3$ individually are alkyl containing 1-3 carbon atoms and cycloalkyl containing 3-5 carbon atoms, R$^4$ is H, alkyl containing 1-4 carbon atoms, and R$^5$ is hydrogen, carbamoyl, N-alkylcarbamoyl (C$_2$-C$_{14}$), N-arylcarbamoyl, N-(substituted aryl)carbamoyl, N-haloalkylcarbamoyl (C$_2$-C$_{12}$), N-carboalkoxyalkylcarbamoyl, N-carboxyalkylcarbamoyl (C$_3$-C$_{14}$), N-alkoxyalkylcarbamoyl (C$_3$-C$_{14}$), N-arylsulfonylcarbamoyl, acyl(C$_1$-C$_{14}$), aroyl, substituted aroyl, alkoxycarbonyl (C$_2$-C$_{14}$), aryloxycarbonyl, hydroxyacyl (C$_2$-C$_8$), alkoxyacyl (C$_3$-C$_9$), alkylthioacyl (C$_3$-C$_9$), alkylsulfonylacyl (C$_3$-C$_7$), N,N-dialkylaminoacyl (C$_4$-C$_{10}$), alkylsulfonyl (C$_1$-C$_{14}$), haloalkylsulfonyl (C$_1$-C$_{14}$), arylsulfonyl, substituted arylsulfonyl, alkyl (C$_1$-C$_{14}$), hydroxyalkyl (C$_1$-C$_8$), alkoxyalkyl (C$_2$-C$_9$), haloalkyl (C$_1$-C$_8$), cycloalkyl (C$_3$-C$_7$), alkenyl (C$_2$-C$_{14}$), cycloalkenyl (C$_5$-C$_7$), alkynyl (C$_2$-C$_{14}$), aryl and substituted aryl.

40. A method according to claim 39 wherein R$^1$ is alkyl containing 1-4 carbon atoms.

41. A method according to claim 40 wherein R$^1$ is methyl.

42. A method according to claim 40 wherein R$^5$ is hydrogen, N-alkylcarbamoyl (C$_2$-C$_{14}$), N-arylcarbamoyl, N-(substituted aryl)carbamoyl, acyl(C$_1$-C$_{14}$), alkoxycarbonyl (C$_2$-C$_{14}$), alkylsulfonyl (C$_1$-C$_{14}$), arylsulfonyl and substituted arylsulfonyl.

43. A method of inhibiting undesired vegetation which comprises applying thereto, in herbicidally effective amounts, a compound selected from the group consisting of compounds having the following generic formula:

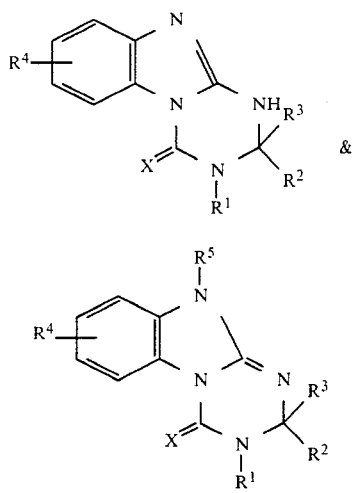

wherein
- $R^1$ is alkyl containing 1-4 carbon atoms,
- $R^2$ and $R^3$ individually are alkyl containing 1-3 carbon atoms and cycloalkyl containing 3-5 carbon atoms,
- $R^4$ is H, alkyl containing 1-4 carbon atoms, and
- $R^5$ is hydrogen, N-alkylcarbamoyl ($C_2$-$C_{14}$), N-arylcarbamoyl, N-(substituted aryl)carbamoyl, acyl ($C_1$-$C_{14}$), alkoxycarbonyl ($C_2$-$C_{14}$), alkylsulfonyl ($C_1$-$C_{14}$), arylsulfonyl and substituted arylsulfonyl.

44. A method according to claim 43 wherein $R^1$ is methyl.

45. A method according to claim 43 wherein $R^4$ is hydrogen.

46. A method of inhibiting undesired vegetation which comprises applying thereto, in herbicidally effective amounts 1,2-dihydro-2,2,3-trimethyl-1,3,5-triazino[1,2-a]benzimidazol-4(3H)-one.

47. A method of inhibiting undesired vegetation which comprises applying thereto, in herbicidally effective amounts 1,2-dihydro-2,3-dimethyl-2-ethyl-1,3,5-triazino[1,2-a]benzimidazol-4(3H)-one.

48. A method of inhibiting undesired vegetation which comprises applying thereto, in herbicidally effective amounts 4-Oxo-2,3,4,10-tetrahydro-N-2,2,3-tetramethyl-1,3,5-triazino[1,2-a]benzimidazole-10-carboxamide.

49. A method of inhibiting undesired vegetation which comprises applying thereto, in herbicidally effective amounts 2-Ethyl-4-oxo-2,3,4,10-tetrahydro-N,2,3-trimethyl-1,3,5-triazino[1,2-a]benzimidazole-10-carboxamide.

50. A method of inhibiting undesired vegetation which comprises applying thereto, in herbicidally effective amounts 2,10-Dihydro-10-(methylsulfonyl)-2,2,3-trimethyl-1,3,5-triazino[1,2-a]benzimidazol-4(3H)-one.

51. A method of inhibiting undesired vegetation which comprises applying thereto, in herbicidally effective amounts 2,10-Dihydro-10-[(4-tolyl)sulfonyl]-2,2,3-trimethyl-1,3,5-triazino[1,2-a]benzimidazol-4(3H)-one.

* * * * *

UNITED STATES PATENT AND TRADEMARK OFFICE
CERTIFICATE OF CORRECTION

PATENT NO. : 4,497,650
DATED : Feb. 5, 1985
INVENTOR(S) : C.E. Ward, R.V. Berthold It is certified that error appears in the above—identified patent and that said Letters Patent is hereby corrected as shown below:

Col. 28, line 23, after "wherein" insert -- X is oxygen or sulfur --.

Col. 30, line 24, after "wherein" insert -- X is oxygen or sulfur --.

Col. 32, line 29, after "wherein" insert -- X is oxygen or sulfur --.

Col. 33, line 22, after "wherein" insert -- X is oxygen or sulfur --.

Signed and Sealed this

Tenth Day of September 1985

[SEAL]

Attest:

DONALD J. QUIGG

*Attesting Officer*   *Acting Commissioner of Patents and Trademarks - Designate*